United States Patent
Nevins et al.

(10) Patent No.: US 6,501,008 B1
(45) Date of Patent: Dec. 31, 2002

(54) MAIZE ENDO-1,3;1,4-β-GLUCANASE NUCLEIC ACID

(75) Inventors: Donald J. Nevins, Davis, CA (US); Carl R. Simmons, Des Moines, IA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/328,965

(22) Filed: Jun. 9, 1999

Related U.S. Application Data

(60) Provisional application No. 60/088,780, filed on Jun. 10, 1998.

(51) Int. Cl.$^7$ .............................. A01H 5/00; A01H 5/10; C12N 15/29; C12N 15/52; C12N 15/82
(52) U.S. Cl. .................... 800/298; 435/320.1; 435/419; 536/23.2; 536/23.6; 800/278; 800/290
(58) Field of Search ............................ 435/69.1, 320.1, 435/419, 468; 536/23.2, 23.6; 800/278, 298, 320.1, 312, 320, 306, 320.3, 314, 320.2

(56) References Cited

PUBLICATIONS

Hatfield, R. and Nevins, D.J. (1986) Purification and properties of an endoglucanase isolated from the cell walls of *Zea mays* seedling cell walls. *Carbohydr. Res.* 148: 265–278.

Hatfield, R. and Nevins, D.J. (1987) Hydrolytic activity and substrate specificity of an endoglucanase from *Zea mays* seedling cell walls. *Plant Physiol.* 83: 203–207.

Hatfield, R. Nevins, D.J. (1988) Plant cell wall proteins: Plant cell wall proteins: partial characterization of maize wall proteins with putative roles in auxin–induced growth. *Plant Cell Physiol.* 29: 713–720.

Hoson, T. and Nevins, D.J. (1989a) β–D–glucan antibodies inhibit auxin–induced cell elongation and changes in the cell wall of *Zea* coleoptile segments. *Plant Physiol.* 90: 1353–1358.

Huber, D.J. and Nevins, D.J. (1979) Autolysis of cell wall β–D–glucan in corn coleoptiles. *Plant Cell Physiol.* 20: 201–212.

Huber, D.J. and Nevins, D.J. (1981a) Partial purification of endo–and exo–β–D–glucanase enzymes from *Zea mays* L. seedlings and their involvement in cell–wall autohydrolysis. *Planta* 151: 206–214.

Huber, D.J. and Nevins, D.J. (1981b) Wall–protein antibodies as inhibitors of growth and autolytic reactions of isolated cell wall. *Physiol. Plant.* 53: 533–539.

Huber, D.J. and Nevins, D.J. (1982) Exoglucanases from *Zea mays* L. seedlings: their role in β–D–glucan hydrolysis and their potential role in extension growth. *Planta* 155: 467–472.

Inouhe, M. and Nevins, D.J. (1991a) Auxin–enhanced glucan autohydrolysis in maize coleoptile cell wall. *Plant Physiol.* 96: 285–290.

Inouhe, M. and Nevins, D.J. (1991b) Inhibition of auxin–induced cell elongation of maize coleoptiles by antibodies specific for cell wall glucanases. *Plant Physiol.* 96: 426–431.

Inouhe, M. and Nevins, D.J. (1997a) Changes in the autolytic activities of maize coleoptile cell walls during coleoptile growth. *Plant Cell Physiol.* 38: 161–167.

Inouhe, M., Hayashi, K., and Nevins, DJ (1999) Polypeptide characteristics and immunological properties of exo–and endoglucanases purified from maize coleoptile cell walls. *J. Plant Physiol* 154(3):334–340.

Inouhe, M., Nevins DJ (1998) Changes in the activities and polypeptide levels of exo–and endoglucanases in cell walls during developmental growth of *Zea mays* coleoptiles. *Plant Cell Physiol* 39(7): 762–768.

Labrador, E. and Nevins, D.J. (1990) An exo–β–D–glucanase derived from *Zea* coleoptile walls with a capacity to elicit cell elongation. *Physiol. Plant.* 77: 479–486.

Luttenegger, D.G. and Nevins, D.J. (1985) Transient nature of a (1–3),(1–4)–β–D–glucan in *Zea mays* coleoptile cell walls. *Plant Physiol.* 77: 175–178.

Simmons, C.R.: The physiology and molecular biology of plant (1–>3)–β–D–glucanase and (1–>3, 1–>4) β–D–glucanases. *Critical Reviews in Plant Sciences* 13, 325–387 (1994).

Masoud, S. A. et al., "Constitutive expression of an inducible B–!, 3–glucanase in alfalfa reduces disease severity caused by the oomycete pathogen Phytophthora magasperma f. sp medicaginis . . . " 1996, Transgenic Research, vol. 5, pp. 313–323.*

Koziel, M. G. et al., "Optimizing expression of transgenes with an emphasis on post–transcriptional events." 1996, Plant Molecular Biology, vol. 32, pp. 393–405.*

Stam, M. et al., "The Silence of Genes in Transgenic Plants." 1997, Annals of Botany, vol. 79, pp. 3–12.*

* cited by examiner

*Primary Examiner*—Elizabeth F. McElwain
*Assistant Examiner*—Russell Kallis
(74) *Attorney, Agent, or Firm*—Townsend and Townsend and Crew LLP

(57) ABSTRACT

The present invention provides, an isolated maize endoglucanase polynucleotide and compositions and methods for modulating (i.e., increasing or decreasing) the total levels of an endoglucanase protein and/or altering their ratios in plants.

11 Claims, No Drawings

MAIZE ENDO-1,3;1,4-β-GLUCANASE NUCLEIC ACID

CROSS REFERENCE RELATED TO APPLICATION

This application claims the benefit of U.S. Provisional Application No. 60/088,780 filed Jun. 10, 1998 and is hereby incorporated by reference.

FIELD OF THE INVENTION

The present invention relates to plant molecular biology. More specifically, the present invention relates to maize exo- and endo-glucanases. Certain rights in the invention may inure to the U.S. Government by way of an N.S.F. grant to Donald J. Nevins.

BACKGROUND OF THE INVENTION

Growth in plants is controlled by the mechanical properties of the cell wall, a structure that otherwise constrains cells and restricts protoplast expansion (Masuda 1990, Sakurai 1991, for review). Changes in the cell wall mechanical properties that impart "loosening" might be achieved through the breakdown and reconstitution of cross-linked polymers in the cell walls. In fact, substantial changes in cell wall components related to cell wall loosening have been reported in many plants (Taiz 1984, Sakurai 1991, Hoson 1993, for reviews). As a parallel to documented changes in cell wall components, specific enzymes capable of degrading cell wall polysaccharides have been identified from the apoplastic compartments of mono- and dicotyledonous plants (Greve and Ordin 1971, Huber and Nevins 1980, 1981a, Labrador and Nevins 1990, Dopico et al. 1990, Nishitani and Tominaga 1992, Hayashi and Ohsumi 1994).

Cereal coleoptile segments, which have served as a model for numerous growth and hormone investigations, undergo molecular changes in non-cellulosic β-glucans coinciding with the initiation of growth. Physical displacement of molecular structures within the wall matrix in response to structural change in the wall is visualized as a means to accommodate pressure driven elongation governed by auxin (Masuda, 1990).

In cereals, most of the effort designed to describe the molecular events in growth has focused on disclosing the role of non-cellulosic β-glucans in auxin-induced growth of coleoptile segments. Auxin causes a specific decrease in the quantity of glucans in the cell walls in vivo, a process coupled with cell elongation of coleoptile segments in oat, barley, rice and maize (Loescher and Nevins 1972, Sakurai and Masuda 1978a, Zarra and Masuda 1979b, Inouhe and Nevins 1991 a). The decrease in the wall glucan content appears to reflect an obligatory chemical basis for cell wall loosening necessary for cell elongation (Sakurai and Masuda 1978b, Sakurai et al. 1979).

Cell wall autohydrolysis, an approach used to disclose the consequences of metabolism mediated by constitutive components, has been employed to identify pertinent enzymes and their substrates. It has been reported that cell walls isolated from maize coleoptiles possess a high autohydrolytic activity (autolysis) specifically directed toward degradation of non-cellulosic β-glucans eventually producing glucose (Huber and Nevins 1979). This process is mediated by wall associated exoglucanase (EC 1.2.3.58, Huber and Nevins 1982) and endoglucanase (Huber and Nevins 1981a, Hat field and Nevins 1986, 1987). The two enzymic activities account for 90% of all the recovered glucanase from maize coleoptile cell walls (Inouhe and Nevins 1991b). The endoglucanase converts the non-cellulosic β-glucans to polymers of an average molecular size of $1-1.5\times10^4$(degree of polymerization of 60–70) and indicates that the endo-glucanase cleaves widely-spaced sites. Auxin is capable of enhancing glucan autolysis in maize coleoptile cell walls (Inouhe and Nevins 1991 a). In addition, polyclonal antibodies specific for cell wall glucanases inhibit the glucan autolysis and auxin-induced growth of maize coleoptile segments (Inouhe and Nevins 1991b). These observations provide evidence to support the idea that the cell wall glucanases have an important role in auxin-induced cell elongation in coleoptile segments.

Notable changes in cell wall glucan content have also been reported in coleoptile tissues developing in intact seedlings of maize (Luttenegger and Nevins 1985), barley (Sakurai and Masuda 1978b), and rice (Zarra and Masuda 1979a). In maize coleoptiles, the non-cellulosic glucans are rapidly synthesized and incorporated into cell walls during early developmental stage but subsequently are degrated to substantially diminished levels after completion of elongation (Luttenegger and Nevins 1985, Inouhe and Nevins 1997a). These data imply that the glucan metabolism mediated by cell wall glucanases is an important phase in coleoptile growth in the intact plant system. However, little is known about changes in cell wall glucanases during coleoptile development, although the timing and spatial distribution of glucanases have been investigated in detail in germinating seeds or leaves of barley seedlings (Mundy and Fincher 1986, Stuart et al. 1986, Slakeski and Fincher 1992a, b).

Diverse glucanases have been isolated from plant sources (Simmons, 1994) and some genes have been identified (Hoj and Fincher, 1995). Information on the precise characteristics of those gene responsible for glucanases in coleoptiles with putative roles in cell extension is, however, not available. Specifically, exo- and endoglucanases from maize have not been isolated or purified until the present invention.

The composition of plant stem material has a strong influence on the feeding quality of major forage crops. Forages contain significant portions of plant cell wall material. From the standpoint of a forage user, the amount and type of plant cell wall is extremely important because it greatly influences how a particular forage will be utilized by animals to produce meat or milk. In silages such as whole plant corn, alfalfa, and the like, the digestibility of the silage is important to ensure availability of the fiber, and/or providing more nutrients per amount of silage at a faster rate. Therefore cell wall constituents are very important in the feeding of animals to produce meat or milk.

SUMMARY OF THE INVENTION

In the present invention, both exo- and endoglucanases were purified and extracted from maize coleoptile cell walls. New maize endoglucanase polynucleotides and related polypeptides were identified. Now by altering expression or modulation of the newly identified maize endoglucanases, one is able to alter the composition of cell walls thereby facilitating cell elongation or expansion and thus altering the growth of a plant or improving kernel growth rates. In addition, alterations in cell wall composition can enhancing silage or forage crop digestibility.

Generally, it is the object of the present invention to provide nucleic acids and proteins relating to endoglucanases. It is an object of the present invention to provide transgenic plants comprising the nucleic acids of the present invention. It is another object of the present invention to provide methods for modulating, in a transgenic plant, the expression of the nucleic acids of the present invention.

Therefore, in one aspect, the present invention relates to an isolated nucleic acid comprising a member selected from the group consisting of (a) a polynucleotide encoding a polypeptide of the present invention; (b) a polynucleotide amplified from a *Zea mays* nucleic acid library using primers designed from the polynucleotides of the present invention; (c) a polynucleotide comprising at least 20 contiguous bases of the polynucleotides of the present invention; (d) a polynucleotide having at least 80% sequence identity to the polynucleotides of the present invention, where sequence identity is determined by Blast 2.0 under default parameters; (e) a polynucleotide comprising at least 25 nucleotide in length which hybridizes under low stringency conditions to the polynucleotides of the present invention; (f) a polynucleotide comprising the sequence set forth in SEQ ID NO: 1; and (g) a polynucleotide complementary to a polynucleotide of (a) through (f). The isolated nucleic acid can be DNA. The isolated nucleic acid can also be RNA.

In another aspect, the present invention relates to vectors comprising the polynucleotides of the present invention. Also the present invention relates to recombinant expression cassettes, comprising a nucleic acid of the present invention operably linked to a promoter.

In another aspect, the present invention is directed to a host cell into which has been introduced the recombinant expression cassette.

In yet another aspect, the present invention relates to a transgenic plant or plant cell comprising a recombinant expression cassette with a promoter operably linked to any of the isolated nucleic acids of the present invention. Preferred plants containing the recombinant expression cassette of the present invention include but are not limited to maize, soybean, sunflower, sorghum, canola, wheat, alfalfa, cotton, rice, barley, and millet. The present invention also provides transgenic seed from the transgenic plant.

In another aspect, the present invention relates to an isolated protein selected from the group consisting of (a) a polypeptide comprising at least 25 contiguous amino acids of SEQ ID NO: 2; (b) a polypeptide comprising at least 80% sequence identity to SEQ ID NO: 2 where the % sequence identity is determined by BLAST 2.0 using default parameters; (c) a polypeptide encoded by a nucleic acid of the present invention; and (d) a polypeptide characterized by SEQ ID NO: 2.

In further aspect, the present invention relates to a method of modulating the level of protein in a plant by introducing into a plant cell a recombinant expression cassette comprising a polynucleotide of the present invention operably linked to a promoter; culturing the plant cell under plant growing conditions to produce a regenerated plant; and inducing expression of the polynucleotide for a time sufficient to modulate the protein of the present invention in the plant. Preferred plants of the present invention include but are not limited to maize, soybean, sunflower, sorghum, canola, wheat, alfalfa, cotton, rice, barley, and millet. The level of protein in the plant can either be increased or decreased.

DEFINITIONS

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes. The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

The term "antibody" includes reference to antigen binding forms of antibodies (e.g., Fab, F(ab)$_2$). The term "antibody" frequently refers to a polypeptide substantially encoded by an immunoglobulin gene or immunoglobulin genes, or fragments thereof which specifically bind and recognize an analyte (antigen). However, while various antibody fragments can be defined in terms of the digestion of an intact antibody, one of skill will appreciate that such fragments may be synthesized de novo either chemically or by utilizing recombinant DNA methodology. Thus, the term antibody, as used herein, also includes antibody fragments such as single chain Fv, chimeric antibodies (i.e., comprising constant and variable regions from different species), humanized antibodies (i.e., comprising a complementarity determining region (CDR) from a non-human source) and heteroconjugate antibodies (e.g., bispecific antibodies).

The term "antigen" includes reference to a substance to which an antibody can be generated and/or to which the antibody is specifically immunoreactive. The specific immunoreactive sites within the antigen are known as epitopes or antigenic determinants. These epitopes can be a linear array of monomers in a polymeric composition—such as amino acids in a protein—or consist of or comprise a more complex secondary or tertiary structure. Those of skill will recognize that all immunogens (i.e., substance capable of eliciting an immune response) are antigens; however some antigens, such as haptens, are not immunogens but may be made immunogenic by coupling to a carrier molecule. An antibody immunologically reactive with a particular antigen can be generated in vivo or by recombinant methods such as selection of libraries of recombinant antibodies in phage or similar vectors. See, e.g., Huse et al., *Science* 246: 1275–1281 (1989); and Ward, et al., *Nature* 341: 544–546 (1989); and Vaughan et al., *Nature Biotech.* 14: 309–314 (1996).

As used herein, "antisense orientation" includes reference to a duplex polynucleotide sequence which is operably linked to a promoter in an orientation where the antisense strand is transcribed. The antisense strand is sufficiently complementary to an endogenous transcription product such that translation of the endogenous transcription product is often inhibited.

As used herein, "chromosomal region" includes reference to a length of chromosome which may be measured by reference to the linear segment of DNA which it comprises. The chromosomal region can be defined by reference to two unique DNA sequences, i.e., markers.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein which encodes a polyp eptide also describes every possible silent variation of the nucleic acid. One of ordinary skill will recognize that each codon in a nucleic acid (except AUG, which is ordinarily the only codon for methionine) can be modified to yield a functionally identical molecule. Accordingly, each silent variation of a nucleic acid which encodes a polypeptide of the present invention is implicit in each described polypeptide sequence and incorporated herein by reference.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the umnmodified polypeptide sequence from which they are derived. For example, substrate specificity, enzyme activity, or ligand/receptor binding is generally at least 30%, 40%, 50%, 60%, 70%, 80%, or 90% of the native protein for it's native substrate. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

See also, Creighton (1984) Proteins W. H. Freeman and Company.

As used herein, "consisting essentially of" means the inclusion of additional sequences to an object polynucleotide where the additional sequences do not selectively hybridize, under stringent hybridization conditions, to the same cDNA as the polynucleotide and where the hybridization conditions include a wash step in 0.1×SSC at 60° C.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as is present in some plant, animal, and fungal mitochondria, the bacterium *Mycoplasma capricolum* (*Proc. Natl. Acad. Sci.* (*USA*), 82: 2306–2309 (1985)), or the ciliate Macronucleus, may be used when the nucleic acid is expressed using these organisms.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17: 477–498 (1989)). Thus, the maize preferred codon for a particular amino acid may be derived from known gene sequences from maize. Maize codon usage for 28 genes from maize plants are listed in Table 4 of Murray et al., supra.

As used herein "full-length sequence" in reference to a specified polynucleotide or its encoded protein means having the entire amino acid sequence of, a native (non-synthetic), endogenous, catalytically active form of the specified protein. A full-length sequence can be determined by size comparison relative to a control which is a native (non-synthetic) endogenous cellular form of the specified nucleic acid or protein. Methods to determine whether a sequence is full-length are well known in the art including such exemplary techniques as northern or western blots, primer extension, S1 protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of MRNA aid in the identification of a polynucleotide as full-length. For example, the consensus sequence ANNNNAUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the expression vector. Host cells may be prokaryotic cells such as *E. coli*, or eukaryotic cells such as yeast, insect, amphibian, or mammalian cells. Preferably, host cells are monocotyledonous or dicotyledenous plant cells. A particularly preferred monocotolydenous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected MRNA).

The terms "isolated" refers to material, such as a nucleic acid or a protein, which is: (1) substantially or essentially free from components which normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a locus in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by non-natural, synthetic (i.e., "manmade") methods performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCTJUS93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

Unless otherwise stated, the term "exo- or endoglucanase nucleic acid" means a nucleic acid comprising a polynucleotide ("exo- or endoglucanase polynucleotide") encoding a exo- or endoglucanase polypeptide. A "exo- or endoglucanase gene" refers to a non-heterologous genomic form of a full-length exo- or endoglucanase polynucleotide.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes in that pair to be followed. A genotype may be defined by use of one or a plurality of markers.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or RNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, Guide to Molecular Cloning Techniques, Methods in Enzymology, Vol. 152, Academic Press, Inc., San Diego, Calif. (Berger); Sambrook et al., Molecular Cloning—A Laboratory Manual, 2nd ed., Vol. 1–3 (1989); and Current Protocols in Molecular Biology, F. M. Ausubel et al., Eds., Current Protocols, a joint venture between Greene Publishing Associates, Inc. and John Wiley & Sons, Inc. (1994 Supplement).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" includes reference to whole plants, plant organs (e.g., leaves, stems, roots, etc.), seeds and plant cells and progeny of same. Plant cell, as used herein includes, without limitation, seeds, suspension cultures, embryos, meristematic regions, callus tissue, leaves, roots, shoots, gametophytes, sporophytes, pollen, and microspores. The class of plants, which can be used in the methods of the invention, is generally as broad as the class of higher plants amenable to transformation techniques, including both monocotyledonous and dicotyledonous plants. Preferred plants include, but are not limited to maize, soybean, sunflower, sorghum, canola, wheat, alfalfa, cotton, rice, barley, and millet. A particularly preferred plant is maize (Zea mays).

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide (s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. Exemplary modifications are described in most basic texts, such as, *Proteins—Structure and Molecular Properties*, 2nd ed., T. E. Creighton, W. H. Freeman and Company, New York (1993). Many detailed reviews are available on this subject, such as, for example, those provided by Wold, F., Posttranslational Protein Modifications: Perspectives and Prospects, pp. 1–12 in *Posttranslational Covalent Modification of proteins*, B. C. Johnson, Ed., Academic Press, New York (1983); Seifter et al., Meth. Enzymol. 182: 626–646 (1990) and Rattan et al., *Protein Synthesis: Posttranslational Modifications and Aging*, Ann. N.Y. Acad. Sci. 663: 48–62 (1992). It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in *E. coli* or other cells, prior to proteolytic processing, almost invariably will be N-formylmethionine. During post-translational modification of the peptide, a methionine residue at the $NH_2$-terminus may be deleted. Accordingly, this invention contemplates the use of both the methionine-containing and the methionineless amino terminal variants of the protein of the invention. In general, as used herein, the term polypeptide encompasses all such modifications, particularly those that are present in polypeptides synthesized by expressing a polynucleotide in a host cell.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether nor not its origin is a plant cell. Exemplary plant promoters include, but are not limited to, those that are obtained from plants, plant viruses, and bacteria which comprise genes expressed in plant cells such Agrobacterium or Rhizobium. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter, which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter, which is active under most environmental conditions.

The term "exo- or endoglucanase polypeptide" refers to one or more amino acid sequences, in glycosylated or non-glycosylated form, involved in the exo- or endoglucanase pathway. The term is also inclusive of fragments, variants, homologs, alleles or precursors (e.g., preproproteins or proproteins) thereof. A "exo- or endoglucanase protein" comprises a exo- or endoglucanase polypeptide.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass known analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The terms "stringent conditions" or "stringent hybridization conditions" includes reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which are up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1× SSC at 60 to 65° C. Unless otherwise stated, in the present application high stringency is defined as hybridization in 4×SSC, 5×Denhardt's (5 g Ficoll, 5 g polyvinypyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267–284 (1984): $T_m$=81.5° C.+16.6 (log M)+0.41 (%GC)−0.61 (% form)−500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatchng results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, N.Y. (1993); and *Current Protocols in Molecular Biology*, Chapter 2, Ausubel, et al., Eds., Greene Publishing and Wiley-Interscience, New York (1995).

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection or transformation of a host cell and into which can be inserted a polynucleotide. Vectors are often replicons. Expression vectors permit transcription and translation of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" means includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of nucleotide and amino acid sequences for comparison are well-known in the art. Optimal alignment of sequences for comparison may be conducted by the local homology algorithm (Best Fit) of Smith and Waterman, *Adv. Appl. Math.* 2: 482 (1981); by the homology alignment algorithm (GAP) of Needleman and Wunsch, *J. Mol. Biol.* 48: 443 (1970); by the search for similarity method (Tfasta and Fasta) of Pearson and Lipman, *Proc. Natl. Acad. Sci.* 85: 2444 (1988); by computerized implementations of these algorithms, including, but not limited to: CLUSTAL in the PC/Gene program by Intelligenetics, Mountain View, Calif., GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73: 237–244 (1988); Higgins and Sharp, *CABIOS* 5: 151–153 (1989); Corpet, et al., *Nucleic Acids Research* 16: 10881–90 (1988); Huang, et al., *Computer Applications in the Biosciences* 8:

155–65 (1992), and Pearson, et al., *Methods in Molecular Biology* 24: 307–331 (1994). The preferred program to use for optimal global alignment of multiple sequences is PileUp (Feng and Doolittle, *Journal of Molecular Evolution*, 25:351–360 (1987) which is similar to the method described by Higgins and Sharp, *CABIOS*, 5:151–153 (1989) and hereby incorporated by reference). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters (Altschul et al., *Nucleic Acids Res.* 25:3389–3402 (1997)). Software for performing BLAST analyses is publicly available, e.g., through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873–5787 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149–163 (1993)) and XNU (Claverie and States, *Comput. Chem.*, 17:191–201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a fall mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4: 11–17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) (i) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) (ii) The terms "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Optionally, optimal alignment is conducted using the homology alignment algorithm of Needleman and Wunsch, *J Mol. Biol.* 48: 443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may differ by conservative amino acid changes.

DETAILED DESCRIPTION OF THE INVENTION

Overview

The present invention provides, compositions and methods for modulating (i.e., increasing or decreasing) the total levels of proteins of the present invention and/or altering their ratios in plants. Thus, the present invention provides utility in such exemplary applications as development and growth of plants, and improving digestibility of silage or forage crops. In particular, the polypeptides of the present invention can be expressed at times, in tissues, and/or in quantities which are uncharacteristic of non-recombinant plants.

The present invention also provides isolated nucleic acid comprising polynucleotides of sufficient length and complementarity to a exo- or endoglucanase gene to use as probes or amplification primers in the detection, quantitation, or isolation of gene transcripts. For example, isolated nucleic acids of the present invention can be used as probes in detecting deficiencies in the level of mRNA in screenings for desired transgenic plants, for detecting mutations in the gene (e.g., substitutions, deletions, or additions), for monitoring upregulation of expression or changes in enzyme activity in screening assays of compounds, for detection of any number of allelic variants (polymorphisms) of the gene, or for use as molecular markers in plant breeding programs. The isolated nucleic acids of the present invention can also be used for recombinant expression of exo- or endoglucanase polypeptides, or for use as immunogens in the preparation and/or screening of antibodies. The isolated nucleic acids of the present invention can also be employed for use in sense or antisense suppression of one or more exo- or endoglucanase genes in a host cell, tissue, or plant. Attachment of chemical agents which bind, intercalate, cleave and/or crosslink to the isolated nucleic acids of the present invention can also be used to modulate transcription or translation. Further, using a primer specific to an insertion sequence (e.g., transposon) and a primer which specifically hybridizes to an isolated nucleic acid of the present invention, one can use nucleic acid amplification to identity insertion sequence inactivated exo- or endoglucanase genes from a cDNA library prepared from insertion sequence mutagenized plants. Progeny seed from the plants comprising the desired inactivated gene can be grown to a plant to study the phenotypic changes characteristic of that inactivation. See, *Tools to Determine the Function of Genes*, 1995 Proceedings of the Fiftieth Annual Corn and Sorghum Industry Research Conference, American Seed Trade Association, Washington, D.C., 1995. Additionally, non-translated 5' or 3' regions of the polynucleotides of the present invention can be used to modulate turnover of heterologous mRNAs and/or protein synthesis. Further, the codon preference characteristic of the polynucleotides of the present invention can be employed in heterologous sequences, or altered in homologous or heterologous sequences, to modulate translational level and/or rates.

The present invention also provides isolated proteins comprising polypeptides including an amino acid sequence from the exo- or endoglucanase polypeptides (e.g., preproenzyme, proenzyme, or enzymes) as disclosed herein. The present invention also provides proteins comprising at least one epitope from a exo- or endoglucanase polypeptide. The proteins of the present invention can be employed in assays for enzyme agonists or antagonists of enzyme function, or for use as immunogens or antigens to obtain antibodies specifically immunoreactive with a protein of the present invention. Such antibodies can be used in assays for expression levels, for identifying and/or isolating nucleic acids of the present invention from expression libraries, or for purification of exo- or endoglucanase polypeptides.

The isolated nucleic acids and proteins of the present invention can be used over a broad range of plant types, particularly monocots such as the species of the family Gramineae including Sorghum bicolor and *Zea mays*. The isolated nucleic acids and proteins of the present invention can also be used in species from the genera: Cucurbita, Rosa, Vitis, Juglans, Fragaria, Lotus, Medicago, Onobrychis, Trifolium, Trigonella, Vigna, Citrus, Linum, Geranium, Manihot, Daucus, Arabidopsis, Brassica, Raphanus, Sinapis, Atropa, Capsicum, Datura, Hyoseyamus, Lycopersicon, Nicotiana, Solanum, Petunia, Digitalis, Majorana, Ciahorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Avena, Hordeum, Secale, Allium, and Triticum.

Nucleic Acids

The present invention provides, among other things, isolated nucleic acids of RNA, DNA, and analogs and/or chimeras thereof, comprising a polynucleotide of the present invention.

A polynucleotide of the present invention is inclusive of:
(a) a polynucleotide encoding a polypeptide of SEQ ID NO: 2 and conservatively modified and polymorphic variants thereof, including exemplary polynucleotides of SEQ ID NO: 1;

(b) a polynucleotide which is the product of amplification from a *Zea mays* nucleic acid library using primer pairs which selectively hybridize under stringent conditions to loci within a polynucleotide selected from the group consisting of SEQ ID NO: 1, wherein the polynucleotide has substantial sequence identity to a polynucleotide selected from the group consisting of SEQ ID NOS: 1;

(c) a polynucleotide which selectively hybridizes to a polynucleotide of (a) or (b);

(d) a polynucleotide having a specified sequence identity with polynucleotides of (a), (b), or (c);

(e) complementary sequences of polynucleotides of (a), (b), (c), or (d); and (f) a polynucleotide comprising at least a specific number of contiguous nucleotides from a polynucleotide of (a), (b), (c), (d), or (e).

A. Polynucleotides Encoding A Protein of an Exo- or Endoglucanase or Conservatively Modified or Polymorphic Variants Thereof The present invention provides isolated nucleic acids comprising a polynucleotide of the present invention, wherein the polynucleotide encodes a polypeptide of the present invention, or conservatively modified or polymorphic variants thereof. Accordingly, the present invention includes polynucleotides of SEQ ID NO: 1, and silent variations of polynucleotides encoding a polypeptide of SEQ ID NO: 2. The present invention further provides isolated nucleic acids comprising polynucleotides encoding conservatively modified variants of a polypeptide of SEQ ID NO: 2. Conservatively modified variants can be used to generate or select antibodies immunoreactive to the non-variant polypeptide. Additionally, the present invention further provides isolated nucleic acids comprising polynucleotides encoding one or more allelic (polymorphic) variants of polypeptides/polynucleotides. Polymorphic variants are frequently used to follow segregation of chromosomal regions in, for example, marker assisted selection methods for crop improvement.

B. Polynucleotides Amplified from a *Zea mays* Nucleic Acid Library

The present invention provides an isolated nucleic acid comprising a polynucleotide of the present invention, wherein the polynucleotides are amplified from a *Zea mays* nucleic acid library. *Zea mays* lines B73, PHRE1, A632, BMS-P2#10, W23, and Mol 7 are known and publicly available. Other publicly known and available maize lines can be obtained from the Maize Genetics Cooperation (Urbana, Ill.). The nucleic acid library may be a cDNA library, a genomic library, or a library generally constructed from nuclear transcripts at any stage of intron processing. cDNA libraries can be normalized to increase the representation of relatively rare cDNAs. In optional embodiments, the cDNA library is constructed using a full-length cDNA synthesis method. Examples of such methods include Oligo-Capping (Maruyama, K. and Sugano, *S. Gene* 138: 171–174, 1994), Biotinylated CAP Trapper (Carninci, P., Kvan, C., et al. *Genomics* 37: 327–336, 1996), and CAP Retention Procedure (Edery, E., Chu, L. L., et al. *Molecular and Cellular Biology* 15: 3363–3371, 1995). cDNA synthesis is often catalyzed at 50–55° C. to prevent formation of RNA secondary structure. Examples of reverse transcriptases that are relatively stable at these temperatures are SuperScript II Reverse Transcriptase (Life Technologies, Inc.), AMV Reverse Transcriptase (Boehringer Mannheim) and Retro-Amp Reverse Transcriptase (Epicentre). Rapidly growing tissues, or rapidly dividing cells are preferably used as mRNA sources. The preferred tissue for the present invention is callus or cell Cultures of the maize line BMS or seedling roots of 1 week old plants of the maize line B73.

The present invention also provides subsequences of the polynucleotides of the present invention. A variety of subsequences can be obtained using primers which selectively hybridize under stringent conditions to at least two sites within a polynucleotide of the present invention, or to two sites within the nucleic acid which flank and comprise a polynucleotide of the present invention, or to a site within a polynucleotide of the present invention and a site within the nucleic acid which comprises it. Primers are chosen to selectively hybridize, under stringent hybridization conditions, to a polynucleotide of the present invention. Generally, the primers are complementary to a subsequence of the target nucleic acid, which they amplify. As those skilled in the art will appreciate, the sites to which the primer pairs will selectively hybridize are chosen such that a single contiguous nucleic acid can be formed under the desired amplification conditions.

In optional embodiments, the primers will be constructed so that they selectively hybridize under stringent conditions to a sequence (or its complement) within the target nucleic acid which comprises the codon encoding the carboxy or amino terminal amino acid residue (i.e., the 3' terminal coding region and 5' terminal coding region, respectively) of the polynucleotides of the present invention. Optionally within these embodiments, the primers will be constructed to selectively hybridize entirely within the coding region of the target polynucleotide of the present invention such that the product of amplification of a cDNA target will consist of the coding region of that cDNA. The primer length in nucleotides is selected from the group of integers consisting of from at least 15 to 50. Thus, the primers can be at least 15, 18, 20, 25, 30, 40, or 50 nucleotides in length. Those of skill will recognize that a lengthened primer sequence can be employed to increase specificity of binding (i.e., annealing) to a target sequence. A non-annealing sequence at the 5' end of a primer (a "tail") can be added, for example, to introduce a cloning site at the terminal ends of the amplicon.

The amplification products can be translated using expression systems well known to those of skill in the art and as discussed, infra. The resulting translation products can be confirmed as polypeptides of the present invention by, for example, assaying for the appropriate catalytic activity (e.g., specific activity and/or substrate specificity), or verifying the presence of one or more linear epitopes, which are specific to a polypeptide of the present invention. Methods for protein synthesis from PCR derived templates are known in the art and available commercially. See, e.g., Amersham Life Sciences, Inc, Catalog '97, p.354.

Methods for obtaining 5' and/or 3' ends of a vector insert are well known in the art. See, e.g., RACE (Rapid Amplification of Complementary Ends) as described in Frohman, M. A., in PCR Protocols: A Guide to Methods and Applications, M. A. Innis, D. H. Gelfand, J. J. Sninsky, T. J. White, Eds. (Academic Press, Inc., San Diego), pp. 28–38 (1990)); see also, U.S. Pat. No. 5,470,722, and *Current Protocols in Molecular Biology*, Unit 15.6, Ausubel, et al., Eds, Greene Publishing and Wiley-Interscience, New York (1995); Frohman and Martin, *Techniques* 1:165 (1989).

C. Polynucleotides Which Selectively Hybridize to a Polynucleotide of (A) or (B)

The present invention provides isolated nucleic acids comprising polynucleotides of the present invention, wherein the polynucleotides selectively hybridize, under selective hybridization conditions, to a polynucleotide of sections (A) or (B) as discussed above. Thus, the polynucleotides of this embodiment can be used for isolating, detecting, and/or quantifying nucleic acids comprising the polynucleotides of (A) or (B). For example, polynucleotides of the present invention can be used to identify, isolate, or amplify partial or full-length clones in a deposited library. In some embodiments, the polynucleotides are genomic or cDNA sequences isolated or otherwise complementary to a cDNA from a dicot or monocot nucleic acid library. Exemplary species of monocots and dicots include, but are not limited to: corn, canola, soybean, cotton, wheat, sorghum, sunflower, oats, sugar cane, millet, barley, and rice. Optionally, the cDNA library comprises at least 80% full-length sequences, preferably at least 85% or 90% full-length sequences, and more preferably at least 95% full-length sequences. The cDNA libraries can be normalized to increase the representation of rare sequences. Low stringency hybridization conditions are typically, but not exclusively, employed with sequences having a reduced sequence identity relative to complementary sequences. Moderate and high stringency conditions can optionally be employed for sequences of greater identity. Low stringency conditions allow selective hybridization of sequences having about 70% sequence identity and can be employed to identify orthologous or paralogous sequences.

D. Polynucleotides Having a Specific Sequence Identity with the Polynucleotides of (A), (B) or (C)

The present invention provides isolated nucleic acids comprising polynucleotides of the present invention, wherein the polynucleotides have a specified identity at the nucleotide level to a polynucleotide as disclosed above in sections (A), (B), or (C), above. The percentage of identity to a reference sequence is at least 60% and, rounded upwards to the nearest integer, can be expressed as an integer selected from the group of integers consisting of from 60 to 99. Thus, for example, the percentage of identity to a reference sequence can be at least 70%, 75%, 80%, 85%, 90%, or 95%.

Optionally, the polynucleotides of this embodiment will encode a polypeptide that will share an epitope with a polypeptide encoded by the polynucleotides of sections (A), (B), or (C). Thus, these polynucleotides encode a first polypeptide which elicits production of antisera comprising antibodies which are specifically reactive to a second polypeptide encoded by a polynucleotide of (A), (B), or (C). However, the first polypeptide does not bind to antisera raised against itself when the antisera has been fully immunosorbed with the first polypeptide. Hence, the polynucleotides of this embodiment can be used to generate antibodies for use in, for example, the screening of expression libraries for nucleic acids comprising polynucleotides of (A), (B), or (C), or for purification of, or in immunoassays for, polypeptides encoded by the polynucleotides of (A), (B), or (C). The polynucleotides of this embodiment embrace nucleic acid sequences which can be employed for selective hybridization to a polynucleotide encoding a polypeptide of the present invention.

Screening polypeptides for specific binding to antisera can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5–100 amino acids long, and often from about 8 to 15 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT patent publication Ser. Nos. 91/17271, 91/18980, 91/19818, and 93/08278. Other systems for generating libraries of peptides have aspects of both in vitro chemical synthesis and recombinant methods. See, PCT Patent publication Ser. Nos. 92/05258, 92/14843, and 96/19256. See also, U.S. Pat. Nos. 5,658,754; and 5,643,768. Peptide display libraries, vectors, and screening kits are commercially available from such suppliers as Invitrogen (Carlsbad, Calif.).

E. Polynucleotides Complementary to the Polynucleotides of (A)–(D)

The present invention provides isolated nucleic acids comprising polynucleotides complementary to the polynucleotides of paragraphs A–D, above. As those of skill in the art will recognize, complementary sequences base-pair throughout the entirety of their length with the polynucleotides of sections (A)–(D) (i.e., have 100% sequence identity over their entire length). Complementary bases associate through hydrogen bonding in double stranded nucleic acids. For example, the following base pairs are complementary: guanine and cytosine; adenine and thymine; and adenine and uracil.

F. Polynucleotides Which are Subsequences of the Polynucleotides of (A)–(E)

The present invention provides isolated nucleic acids comprising polynucleotides which comprise at least 15 contiguous bases from the polynucleotides of sections (A) through (E) as discussed above. The length of the polynucleotide is given as an integer selected from the group consisting of from at least 15 to the length of the nucleic acid sequence from which the polynucleotide is a subsequence of. Thus, for example, polynucleotides of the present invention are inclusive of polynucleotides comprising at least 15, 20, 25, 30, 40, 50, 60, 75, or 100 contiguous nucleotides in length from the polynucleotides of (A)–(E). Optionally, the number of such subsequences encoded by a polynucleotide of the instant embodiment can be any integer selected from the group consisting of from 1 to 20, such as 2, 3, 4, or 5. The subsequences can be separated by any integer of nucleotides from 1 to the number of nucleotides in the sequence such as at least 5, 10, 15, 25, 50, 100, or 200 nucleotides.

The subsequences of the present invention can comprise structural characteristics of the sequence from which it is derived. Alternatively, the subsequences can lack certain structural characteristics of the larger sequence from which it is derived such as a poly (A) tail. Optionally, a subsequence from a polynucleotide encoding a polypeptide having at least one linear epitope in common with a prototype polypeptide sequence as provided in (a), above, may encode an epitope in common with the prototype sequence. Alternatively, the subsequence may not encode an epitope in common with the prototype sequence but can be used to isolate the larger sequence by, for example, nucleic acid hybridization with the sequence from which it's derived. Subsequences can be used to modulate or detect gene expression by introducing into the subsequences compounds which bind, intercalate, cleave and/or crosslink to nucleic acids. Exemplary compounds include acridine, psoralen, phenanthroline, naphthoquinone, daunomycin or chloroethylaminoaryl conjugates.

Construction of Nucleic Acids

The isolated nucleic acids of the present invention can be made using (a) standard recombinant methods, (b) synthetic techniques, or combinations thereof. In some embodiments, the polynucleotides of the present invention will be cloned, amplified, or otherwise constructed from a monocot. In preferred embodiments the monocot is *Zea mays*. Particularly preferred is the use of *Zea mays* tissue.

The nucleic acids may conveniently comprise sequences in addition to a polynucleotide of the present invention. For example, a multi-cloning site comprising one or more endonuclease restriction sites may be inserted into the nucleic acid to aid in isolation of the polynucleotide. Also, translatable sequences may be inserted to aid in the isolation of the translated polynucleotide of the present invention. For example, a hexa-histidine marker sequence provides a convenient means to purify the proteins of the present invention. The nucleic acid of the present invention—excluding the polynucleotide sequence—is optionally a vector, adapter, or linker for cloning and/or expression of a polynucleotide of the present invention. Additional sequences may be added to such cloning and/or expression sequences to optimize their function in cloning and/or expression, to aid in isolation of the polynucleotide, or to improve the introduction of the polynucleotide into a cell. Typically, the length of a nucleic acid of the present invention less the length of its polynucleotide of the present invention is less than 20 kilobase pairs, often less than 15 kb, and frequently less than 10 kb. Use of cloning vectors, expression vectors, adapters, and linkers is well known in the art. Exemplary nucleic acids include such vectors as: M13, lambda ZAP Express, lambda ZAP II, lambda gt10, lambda gt11, pBK-CMV, pBK-RSV, pBluescript II, lambda DASH II, lambda EMBL 3, lambda EMBL 4, pWE15, SuperCos 1, SurfZap, Uni-ZAP, pBC, pBS+/−, pSG5, pBK, pCR-Script, pET, pSPUTK, p3' SS, pOPRSVI CAT, pOPI3 CAT, pXT1, pSG5, pPbac, pMbac, pMC1neo, pOG44, pOG45, pFRTβ GAL, pNEOβ GAL, pRS403, pRS404, pRS405, pRS406, pRS413, pRS414, pRS415, pRS416, lambda MOSSlox, and lambda MOSElox. For a description of various nucleic acids see, for example, Stratagene Cloning Systems, Catalogs 1995, 1996, 1997 (La Jolla, Calif.); and, Amersham Life Sciences, Inc, Catalog '97 (Arlington Heights, Ill.).

A. Recombinant Methods for Constructing Nucleic Acids

The isolated nucleic acid compositions of this invention, such as RNA, cDNA, genomic DNA, or a hybrid thereof, can be obtained from plant biological sources using any number of cloning methodologies known to those of skill in the art. In some embodiments, oligonucleotide probes which selectively hybridize, under stringent conditions, to the polynucleotides of the present invention are used to identify the desired sequence in a cDNA or genomic DNA library. While isolation of RNA, and construction of cDNA and genomic libraries is well known to those of ordinary skill in the art, the following highlights some of the methods employed.

A1. mRNA Isolation and Purification

Total RNA from plant cells comprises such nucleic acids as mitochondrial RNA, chloroplastic RNA, rRNA, tRNA, hnRNA and mRNA. Total RNA preparation typically involves lysis of cells and removal of proteins, followed by precipitation of nucleic acids. Extraction of total RNA from plant cells can be accomplished by a variety of means. Frequently, extraction buffers include a strong detergent such as SDS and an organic deanturant such as guanidinium isothiocyanate, guanidine hydrochloride or phenol. Following total RNA isolation, poly(A)$^+$ mRNA is typically purified from the remainder RNA using oligo(dT) cellulose. Exemplary total RNA and mRNA isolation protocols are described in *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995). Total RNA and mRNA isolation kits are commercially available from vendors such as Stratagene (La Jolla, Calif.), Clonetech (Palo Alto, Calif.), Pharmacia (Piscataway, N.J.), and 5' -3' (Paoli, Pa.). See also, U.S. Pat. Nos. 5,614,391; and, 5,459,253. The mRNA can be fractionated into populations with size ranges of about 0.5, 1.0, 1.5, 2.0, 2.5 or 3.0 kb. The cDNA synthesized for each of these fractions can be size selected to the same size range as its mRNA prior to vector insertion. This method helps eliminate truncated cDNA formed by incompletely reverse transcribed mRNA.

A2. Construction of a cDNA Library

Construction of a cDNA library generally entails five steps. First, first strand cDNA synthesis is initiated from a poly(A)$^+$ mRNA template using a poly(dT) primer or random hexanucleotides. Second, the resultant RNA-DNA hybrid is converted into double stranded CDNA, typically by a combination of RNAse H and DNA polymerase I (or Klenow fragment). Third, the termini of the double stranded cDNA are ligated to adaptors. Ligation of the adaptors will produce cohesive ends for cloning. Fourth, size selection of the double stranded CDNA eliminates excess adaptors and primer fragments, and eliminates partial CDNA molecules due to degradation of mRNAs or the failure of reverse transcriptase to synthesize complete first strands. Fifth, the cDNAs are ligated into cloning vectors and packaged. CDNA synthesis protocols are well known to the skilled artisan and are described in such standard references as: *Plant Molecular Biology: A Laboratory Manual*, Clark, Ed., Springer-Verlag, Berlin (1997); and, *Current Protocols in Molecular Biology*, Ausubel, et al., Eds., Greene Publishing and Wiley-Interscience, New York (1995). cDNA synthesis kits are available from a variety of commercial vendors such as Stratagene or Phamacia.

A number of cDNA synthesis protocols have been described which provide substantially pure full-length cDNA libraries. Substantially pure full-length cDNA libraries are constructed to comprise at least 90%, and more preferably at least 93% or 95% full-length inserts amongst clones containing inserts. The length of insert in such libraries can be from 0 to 8, 9, 10, 11, 12, 13, or more kilobase pairs. Vectors to accommodate inserts of these sizes are known in the art and available commercially. See, e.g., Stratagene's lambda ZAP Express (cDNA cloning vector with 0 to 12 kb cloning capacity).

An exemplary method of constructing a greater than 95% pure full-length cDNA library is described by Caminci et al., *Genomics*, 37:327–336 (1996). In that protocol, the cap-structure of eukaryotic mRNA is chemically labeled with biotin. By using streptavidin-coated magnetic beads, only the full-length first-strand cDNA/mRNA hybrids are selectively recovered after RNase I treatment. The method provides a high yield library with an unbiased representation of the starting mRNA population. Other methods for producing full-length libraries are known in the art. See, e.g., Edery et al., *Mol. Cell Biol.*, 15(6): 3363–3371 (1995); and, PCT Application WO 96/34981.

A3. Normalized or Subtracted cDNA Libraries

A non-normalized cDNA library represents the mRNA population of the tissue it was made from. Since unique clones are out-numbered by clones derived from highly expressed genes their isolation can be laborious. Normalization of a cDNA library is the process of creating a library in which each clone is more equally represented.

A number of approaches to normalize cDNA libraries are known in the art. One approach is based on hybridization to genomic DNA. The frequency of each hybridized cDNA in the resulting normalized library would be proportional to that of each corresponding gene in the genomic DNA. Another approach is based on kinetics. If cDNA reannealing follows second-order kinetics, rarer species anneal less rapidly and the remaining single-stranded fraction of cDNA becomes progressively more normalized during the course of the hybridization. Specific loss of any species of cDNA, regardless of its abundance, does not occur at any Cot value. Construction of normalized libraries is described in Ko, *Nucl. Acids. Res.*, 18(19):5705–5711 (1990); Patanjali et al, *Proc. Natl. Acad. U.S.A.*, 88:1943–1947 (1991); U.S. Pat. Nos. 5,482,685, and 5,637,685. In an exemplary method described by Soares et al., normalization resulted in reduction of the abundance of clones from a range of four orders of magnitude to a narrow range of only 1 order of magnitude. *Proc. Natl. Acad. Sci. USA*, 91:9228–9232 (1994).

Subtracted cDNA libraries are another means to increase the proportion of less abundant cDNA species. In this procedure, cDNA prepared from one pool of mRNA is depleted of sequences present in a second pool of mRNA by hybridization. The cDNA:mRNA hybrids are removed and the remaining un-hybridized CDNA pool is enriched for sequences unique to that pool. See, Foote et al. in, *Plant Molecular Biology: A Laboratory Manual*, Clark, Ed., Springer-Verlag, Berlin (1997); Kho and Zarbl, *Technique*, 3(2):58–63 (1991); Sive and St. John, *Nucl. Acids Res.*, 16(22):10937 (1988); *Current Protocols in Molecular Biology*, Ausubel, et al., Eds., Greene Publishing and Wiley-Interscience, New York (1995); and, Swaroop et al., *Nucl. Acids Res.*, 19)8):1954 (1991). cDNA subtraction kits are commercially available. See, e.g., PCR-Select (Clontech).

A4. Construction of a Genomic Library

To construct genomic libraries, large segments of genomic DNA are generated by random fragmentation, e.g. using restriction endonucleases, and are ligated with vector DNA to form concatemers that can be packaged into the appropriate vector. Methodologies to accomplish these ends, and sequencing methods to verify the sequence of nucleic acids are well known in the art. Examples of appropriate molecular biological techniques and instructions sufficient to direct persons of skill through many construction, cloning, and screening methodologies are found in Sambrook, et al., *Molecular Cloning: A Laboratory Manual*, 2nd Ed., Cold Spring Harbor Laboratory Vols. 1–3 (1989), Methods in Enzymology, Vol. 152: *Guide to Molecular Cloning Techniques*, Berger and Kimmel, Eds., San Diego: Academic Press, Inc. (1987), *Current Protocols in Molecular Biology*, Ausubel, et al., Eds., Greene Publishing and Wiley-Interscience, New York (1995); *Plant Molecular Biology: A Laboratory Manual*, Clark, Ed., Springer-Verlag, Berlin (1997). Kits for construction of genomic libraries are also commercially available.

A5. Nucleic Acid Screening and Isolation Methods

The cDNA or genomic library can be screened using a probe based upon the sequence of a polynucleotide of the present invention such as those disclosed herein. Probes may be used to hybridize with genomic DNA or cDNA sequences to isolate homologous genes in the same or different plant species. Those of skill in the art will appreciate that various degrees of stringency of hybridization can be employed in the assay; and either the hybridization or the wash medium can be stringent. As the conditions for hybridization become more stringent, there must be a greater degree of complementarity between the probe and the target for duplex formation to occur. The degree of stringency can be controlled by temperature, ionic strength, pH and the presence of a partially denaturing solvent such as formamide. For example, the stringency of hybridization is conveniently varied by changing the polarity of the reactant solution through manipulation of the concentration of formamide within the range of 0% to 50%. The degree of complementarity (sequence identity) required for detectable binding will vary in accordance with the stringency of the hybridization medium and/or wash medium. The degree of complementarity will optimally be 100 percent; however, it should be understood that minor sequence variations in the probes and primers may be compensated for by reducing the stringency of the hybridization and/or wash medium.

The nucleic acids of interest can also be amplified from nucleic acid samples using amplification techniques. For instance, polymerase chain reaction (PCR) technology can be used to amplify the sequences of polynucleotides of the present invention and related genes directly from genomic DNA or cDNA libraries. PCR and other in vitro amplification methods may also be useful, for example, to clone nucleic acid sequences that code for proteins to be expressed, to make nucleic acids to use as probes for detecting the presence of the desired mRNA in samples, for nucleic acid sequencing, or for other purposes. Examples of techniques sufficient to direct persons of skill through in vitro amplification methods are found in Berger, Sambrook, and Ausubel, as well as Mullis et al., U.S. Pat. No. 4,683,202 (1987); and, PCR *Protocols A Guide to Methods and Applications*, Innis et al., Eds., Academic Press Inc., San Diego, Calif. (1990). Commercially available kits for genomic PCR amplification are known in the art. See, e.g., Advantage-GC Genomic PCR Kit (Clontech). The T4 gene 32 protein (Boehringer Mannheim) can be used to improve yield of long PCR products.

PCR-based screening methods have also been described. Wilfinger et al. describe a PCR-based method in which the longest cDNA is identified in the first step so that incomplete clones can be eliminated from study. *BioTechniques*, 22(3): 481–486 (1997). In that method, a primer pair is synthesized with one primer annealing to the 5' end of the sense strand of the desired cDNA and the other primer to the vector. Clones are pooled to allow large-scale screening. By this procedure, the longest possible clone is identified amongst candidate clones. Further, the PCR product is used solely as a diagnostic for the presence of the desired cDNA and does not utilize the PCR product itself. Such methods are particularly effective in combination with a full-length cDNA construction methodology, supra.

B. Synthetic Methods for Constructing Nucleic Acids

The isolated nucleic acids of the present invention can also be prepared by direct chemical synthesis by methods such as the phosphotriester method of Narang et al., *Meth. Enzymol.* 68: 90–99 (1979); the phosphodiester method of Brown et al., *Meth. Enzymol.* 68: 109–151 (1979); the diethylphosphoramidite method of Beaucage et al., *Tetra. Lett.* 22: 1859–1862 (1981); the solid phase phosphoramidite triester method described by Beaucage and Caruthers, *Tetra. Letts.* 22(20): 1859–1862 (1981), e.g., using an automated synthesizer, e.g., as described in Needham-VanDevanter et al., *Nucleic Acids Res.*, 12: 6159–6168 (1984); and, the solid support method of U.S. Pat. No. 4,458,066. Chemical synthesis generally produces a single stranded oligonucleotide. This may be converted into double stranded DNA by hybridization with a complementary sequence, or by polymerization with a DNA polymerase using the single strand as a template. One of skill will recognize that while chemical synthesis of DNA is limited to sequences of about 100 bases, longer sequences may be obtained by the ligation of shorter sequences.

The present invention further provides recombinant expression cassettes comprising a nucleic acid of the present invention. A nucleic acid sequence coding for the desired polynucleotide of the present invention, for example a cDNA or a genomic sequence encoding a full length polypeptide of the present invention, can be used to construct a recombinant expression cassette which can be introduced into the desired host cell. A recombinant expression cassette will typically comprise a polynucleotide of the present invention operably linked to transcriptional initiation regulatory sequences which will direct the transcription of the polynucleotide in the intended host cell, such as tissues of a transformed plant.

For example, plant expression vectors may include (1) a cloned plant gene under the transcriptional control of 5' and 3' regulatory sequences and (2) a dominant selectable marker. Such plant expression vectors may also contain, if desired, a promoter regulatory region (e.g., one conferring inducible or constitutive, environmentally- or developmentally-regulated, or cell- or tissue-specific/ selective expression), a transcription initiation start site, a ribosome binding site, an RNA processing signal, a transcription termination site, and/or a polyadenylation signal.

A number of promoters can be used in the practice of the invention. A plant promoter fragment can be employed which will direct expression of a polynucleotide of the present invention in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'- promoter derived from T-DNA of *Agrobacterium tumefaciens*, the ubiquitin 1 promoter (Christensen, et al. *Plant Mol Biol* 18, 675–689 (1992); Bruce, et al., *Proc Natl Acad Sci USA* 86, 9692–9696 (1989)), the Smas promoter, the cinnamyl alcohol dehydrogenase promoter (U.S. Pat. No. 5,683,439), the Nos promoter, the pEmu promoter, the rubisco promoter, the GRP1-8 promoter, the Rysn7 promoter (WO97/47756) and other transcription initiation regions from various plant genes known to those of skill. The preferred promoter for expression of the polynucleotides of the present invention in a monocot is the ubiquitin 1 promoter.

Where low level expression is desired, weak promoters will be used. It is recognized that weak inducible promoters may be used. Additionally, either a weak constitutive or a weak tissue specific promoter may be used. Generally, by "weak promoter" is intended a promoter that drives expression of a coding sequence at a low level. By low level is intended at levels of about 1/1000 transcripts to about 1/100,000 transcripts to about 1/500,000 transcripts. Alternatively, it is recognized that weak promoters also encompass promoters that are expressed in only a few cells and not in others to give a total low level of expression. Such weak constitutive promoters include, for example, the core promoter of the Rsyn7 (WO 97/44756), the core 35S CaMV promoter, and the like. Where a promoter is expressed at unacceptably high levels, portions of the promoter sequence can be deleted or modified to decrease expression levels. Additionally, to obtain a varied series in the level of expression, one can also make a set of transgenic plants containing the polynucleotides of the present invention with a strong constitutive promoter, and then rank the transgenic plants according to the observed level of expression. The transgenic plants will show a variety in performance, from high expression to low expression. Factors such as chromosomal position effect, cosuppression, and the like will affect the expression of the polynucleotide.

Alternatively, the plant promoter can direct expression of a polynucleotide of the present invention under environmental control. Such promoters are referred to here as "inducible" promoters. Environmental conditions that may effect transcription by inducible promoters include pathogen attack, anaerobic conditions, or the presence of light. Examples of inducible promoters are the Adh1 promoter, which is inducible by hypoxia or cold stress, the Hsp70 promoter, which is inducible by heat stress, and the PPDK promoter, which is inducible by light. Examples of pathogen-inducible promoters include those from proteins, which are induced following infection by a pathogen; e.g., PR proteins, SAR proteins, beta-1,3-glucanase, chitinase, etc. See, for example, Redolfi, et al., *Neth J. Plant Pathol.* 89:245–254 (1983); Uknes, et al., *The Plant Cell* 4:645–656 (1992); Van Loon, *Plant Mol. Virol.* 4:111–116 (1985); copending U.S. application Ser. No. 60/076,100, filed Feb. 26, 1998; and copending U.S. application Ser. No. 60/079, 648, filed Mar. 27, 1998.

Of interest are promoters that are expressed locally at or near the site of pathogen infection. See, for example, Marineau, et al., *Plant Mol Biol* 9:335–342 (1987); Matton, et al., *Molecular Plant-Microbe Interactions* 2:325–342 (1987); Somsisch et al., *Proc Natl Acad Sci USA* 83:2427–2430 (1986); Somssich et al., *Mole Gen Genetics* 2:93–98 (1988); Yang, *Proc Natl Acad Sci USA* 93:14972–14977. See also, Chen, et al., *Plant J* 10:955–966 (1996); Zhang and Sing, *Proc Natl Acad Sci USA* 91:2507–2511 (1994); Warner, et al., *Plant J* 3:191–201 (1993); and Siebertz, et al, *Plant Cell* 1:961–968 (1989), all of which are herein incorporated by reference. Of particular interest is the inducible promoter for the maize PRms gene, whose expression is induced by the pathogen *Fusarium moniliforme* (see, for example, Cordero, et al., *Physiol Molec Plant Path* 41:189–200 (1992) and is herein incorporated by reference.

Additionally, as pathogens find entry into plants through wounds or insect damage, a wound inducible promoter may be used in the constructs of the invention. Such wound inducible promoters include potato proteinase inhibitor (pin II) gene (Ryan, *Annu Rev Phytopath* 28:425–449 (1990); Duan, et a., *Nat Biotech* 14:494–498 (1996)); wun1 and wun 2, U.S. Pat. No. 5,428,148; win1 and win2 (Stanford, et al, *Mol Gen Genet* 215:200–208 (1989)); systemin (McGurl, et al., *Science* 225:1570–1573 (1992)); WIP1 (Rohmeier, et al., *Plant Mol Biol* 22:783–792 (1993); Eckelkamp, et al., *FEB Letters* 323:73–76 (1993)); MPI gene (Corderok, et al., *The Plant J* 6(2):141–150(1994)); and the like, herein incorporated by reference.

Examples of promoters under developmental control include promoters that initiate transcription only, or preferentially, in certain tissues, such as leaves, roots, fruit, seeds, stalks, or flowers. Exemplary promoters include the anther specific promoter 5126 (U.S. Pat. Nos. 5,689,049 and 5,689,051), glob-1 promoter, and gamma-zein promoter. An exemplary promoter for leaf- and stalk-preferred expression is MS8–15 (WO 98/00533). Examples of seed-preferred promoters included, but are not limited to, 27 kD gamma zein promoter and waxy promoter (Boronat, et al., *Plant Sci*, 47:95–102 (1986); Reina, et al., *Nucleic Acids Res* 18(21) :6426 (1990); and Kloesgen, et al., *Mol Gen Genet* 203: 237–244 (1986)). Promoters that express in the embryo, pericarp, and endosperm are disclosed in U.S. application Ser. Nos. 60/097,233 filed Aug. 20, 1998 and U.S. application Ser. No. 60/098,230 filed Aug. 28, 1998. The disclosures of each of these are incorporated herein by reference in their entirety. The operation of a promoter may also vary depending on its location in the genome. Thus, a developmentally regulated promoter may become fully or partially constitutive in certain locations. A developmentally regulated promoter can also be modified, if necessary, for weak expression.

Both heterologous and non-heterologous (i.e., endogenous) promoters can be employed to direct expression of the nucleic acids of the present invention. These promoters can also be used, for example, in recombinant expression cassettes to drive expression of antisense nucleic acids to reduce, increase, or alter concentration and/or composition of the proteins of the present invention in a desired tissue. Thus, in some embodiments, the nucleic acid construct will comprise a promoter functional in a plant cell, such as in Zea mays, operably linked to a polynucleotide of the present invention. Promoters useful in these embodiments include the endogenous promoters driving expression of a polypeptide of the present invention.

In some embodiments, isolated nucleic acids which serve as promoter or enhancer elements can be introduced in the appropriate position (generally upstream) of a non-heterologous form of a polynucleotide of the present invention so as to up or down regulate expression of a polynucleotide of the present invention. For example, endogenous promoters can be altered in vivo by mutation, deletion, and/or substitution (see, Kmiec, U.S. Pat. No. 5,565,350; Zarling et al., PCT/US93/03868), or isolated promoters can be introduced into a plant cell in the proper orientation and distance from a gene of the present invention so as to control the expression of the gene. Gene expression can be modulated under conditions suitable for plant growth so as to alter the total concentration and/or alter the composition of the polypeptides of the present invention in plant cell. Thus, the present invention provides compositions, and methods for making, heterologous promoters and/or enhancers operably linked to a native, endogenous (i.e., non-heterologous) form of a polynucleotide of the present invention.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added can be derived from, for example, the nopaline synthase or octopine synthase genes, or alternatively from another plant gene, or less preferably from any other eukaryotic gene.

An intron sequence can be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold. Buchmnan and Berg, *Mol. Cell Biol.* 8:4395–4405(1988); Callis et al., *Genes Dev.* 1: 1183–1200(1987). Such intron enhancement of gene expression is typically greatest when placed near the 5' end of the transcription unit. Use of maize introns Adh1-S intron 1, 2, and 6, the Bronze-1 intron are known in the art. See generally, *The Maize Handbook*, Chapter 116, Freeling and Walbot, Eds., Springer, N.Y. (1994).

The vector comprising the sequences from a polynucleotide of the present invention will typically comprise a marker gene, which confers a selectable phenotype on plant cells. Usually, the selectable marker gene will encode antibiotic resistance, with suitable genes including genes coding for resistance to the antibiotic spectinomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance, genes coding for resistance to herbicides which act to inhibit the action of acetolactate synthase (ALS), in particular the sulfonylurea-type herbicides (e.g., the acetolactate synthase (ALS) gene containing mutations leading to such resistance in particular the S4 and/or Hra mutations), genes coding for resistance to herbicides which act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Typical vectors useful for expression of genes in higher plants are well known in the art and include vectors derived from the tumor-inducing (Ti) plasmid of *Agrobacterium tumefaciens* described by Rogers et al., Meth. In Enzymol., 153:253–277 (1987). These vectors are plant integrating vectors in that on transformation, the vectors integrate a portion of vector DNA into the genome of the host plant. Exemplary *A. tumefaciens* vectors useful herein are plasmids pKYLX6 and pKYLX7 of Schardl et al., *Gene*, 61:1–11 (1987) and Berger et al., *Proc. Natl. Acad. Sci. U.S.A.*, 86:8402–8406 (1989). Another useful vector herein is plasmid pBI101.2 that is available from Clontech Laboratories, Inc. (Palo Alto, Calif.).

A polynucleotide of the present invention can be expressed in either sense or anti-sense orientation as desired. It will be appreciated that control of gene expression in either sense or anti-sense orientation can have a direct impact on the observable plant characteristics. Antisense technology can be conveniently used to inhibit gene expression in plants. To accomplish this, a nucleic acid segment from the desired gene is cloned and operably linked to a promoter such that the anti-sense strand of RNA will be transcribed. The construct is then transformed into plants and the antisense strand of RNA is produced. In plant cells, it has been shown that antisense RNA inhibits gene expression by preventing the accumulation of mRNA which encodes the enzyme of interest, see, e.g., Sheehy et al.,*Proc. Nat'l. Acad. Sci.* (*USA*) 85: 8805–8809 (1988); and Hiatt et al., U.S. Pat. No. 4,801,340.

Another method of suppression is sense suppression. Introduction of nucleic acid configured in the sense orientation has been shown to be an effective means by which to block the transcription of target genes. For an example of the use of this method to modulate expression of endogenous genes see, Napoli et al., *The Plant Cell* 2: 279–289 (1990) and U.S. Pat. No. 5,034,323.

Catalytic RNA molecules or ribozymes can also be used to inhibit expression of plant genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs. The design and use of target RNA-specific ribozymes is described in Haseloff et al., *Nature* 334: 585–591 (1988).

A variety of cross-linking agents, alkylating agents and radical generating species as pendant groups on polynucleotides of the present invention can be used to bind, label, detect, and/or cleave nucleic acids. For example, Vlassov, V. V., et al., *Nucleic Acids Res* (1986) 14:4065–4076, describe covalent bonding of a single-stranded DNA fragment with alkylating derivatives of nucleotides complementary to target sequences. A report of similar work by the same group is that by Knorre, D. G., et al., *Biochimie* (1985) 67:785–789. Iverson and Dervan also showed sequence-specific cleavage of single-stranded DNA mediated by incorporation of a modified nucleotide which was capable of activating cleavage (*J Am Chem Soc* (1987) 109:1241–1243). Meyer, R. B., etal., *J Am Chem Soc* (1989) 111:8517–8519, effect covalent crosslinking to a target nucleotide using an alkylating agent complementary to the single-stranded target nucleotide sequence. A photoactivated crosslinking to single-stranded oligonucleotides mediated by psoralen was disclosed by Lee, B. L., et al., *Biochemistry* (1988) 27:3197–3203. Use of crosslinking in triple-helix forming probes was also disclosed by Home, et al., *J Am Chem Soc* (1990) 112:2435–2437. Use of N4, N4-ethanocytosine as an alkylating agent to crosslink to single-stranded oligonucleotides has also been described by Webb and Matteucci, *J Am Chem Soc* (1986) 108:2764–2765; *Nucleic Acids Res* (1986) 14:7661–7674; Feteritz et al., *J. Am. Chem. Soc.* 113:4000 (1991). Various compounds to bind, detect, label, and/or cleave nucleic acids are known in the art. See, for example, U.S. Pat. Nos. 5,543,507; 5,672,593; 5,484,908; 5,256,648; and, 5,681,941.

Proteins

The isolated proteins of the present invention comprise a polypeptide having at least 10 amino acids encoded by any one of the polynucleotides of the present invention as discussed more fully, supra, or polypeptides which are conservatively modified variants thereof. Exemplary polypeptide sequences are provided in SEQ ID NO: 2. The proteins of the present invention or variants thereof can comprise any number of contiguous amino acid residues from a polypeptide of the present invention, wherein that number is selected from the group of integers consisting of from 10 to the number of residues in a full-length endoglucanase polypeptide. Optionally, this subsequence of contiguous amino acids is at least 15, 20, 25, 30, 35, or 40 amino acids in length, often at least 50, 60, 70, 80, or 90 amino acids in length. Further, the number of such subsequences can be any integer selected from the group consisting of from 1 to 20, such as 2, 3, 4, or 5.

As those of skill will appreciate, the present invention includes catalytically active polypeptides of the present invention (i.e., enzymes). Catalytically active polypeptides have a specific activity at least 20%, 30%, or 40%, and preferably at least 50%, 60%, or 70%, and most preferably at least 80%, 90%, or 95% that of the native (non-synthetic), endogenous polypeptide. Further, the substrate specificity ($k_{cat}/K_m$) is optionally substantially similar to the native (non-synthetic), endogenous polypeptide. Typically, the $K_m$ will be at least 30%, 40%, or 50%, that of the native (non-synthetic), endogenous polypeptide; and more preferably at least 60%, 70%, 80%, or 90%. Methods of assaying and quantifying measures of enzymatic activity and substrate specificity ($k_{cat}/K_m$), are well known to those of skill in the art.

Generally, the proteins of the present invention will, when presented as an immunogen, elicit production of an antibody specifically reactive to a polypeptide of the present invention encoded by a polynucleotide of the present invention as described, supra. Exemplary polypeptides include those which are full-length, such as those disclosed in SEQ ID NO: 2. Further, the proteins of the present invention will not bind to antisera raised against a polypeptide of the present invention which has been fully immunosorbed with the same polypeptide. Immunoassays for determining binding are well known to those of skill in the art. A preferred immunoassay is a competitive immunoassay as discussed, infra. Thus, the proteins of the present invention can be employed as immunogens for constructing antibodies immunoreactive to a protein of the present invention for such exemplary utilities as immunoassays or protein purification techniques. The endoglucanase polynucleotide sequences contain the 27 nucleotide or 9 amino acid endoglucanase signature sequence. The conserved consensus pattern would be particularly useful in the production of antibodies.

Expression of Proteins in Host Cells

Using the nucleic acids of the present invention, one may express a protein of the present invention in a recombinantly engineered cell such as bacteria, yeast, insect, mammalian, or preferably plant cells. The cells produce the protein in a non-natural condition (e.g., in quantity, composition, location, and/or time), because they have been genetically altered through human intervention to do so.

It is expected that those of skill in the art are knowledgeable in the numerous expression systems available for expression of a nucleic acid encoding a protein of the present invention. No attempt to describe in detail the various methods known for the expression of proteins in prokaryotes or eukaryotes will be made.

In brief summary, the expression of isolated nucleic acids encoding a protein of the present invention will typically be achieved by operably linking, for example, the DNA or cDNA to a promoter (which is either constitutive or inducible), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high level expression of a cloned gene, it is desirable to construct expression vectors which contain, at the minimum, a strong promoter to direct transcription, a ribosome binding site for translational initiation, and a transcription/translation terminator. One of skill would recognize that modifications can be made to a protein of the present invention without diminishing its biological activity. Some modifications may be made to facilitate the cloning, expression, or incorporation of the targeting molecule into a fusion protein. Such modifications are well known to those of skill in the art and include, for example, a methionine added at the amino terminus to provide an initiation site, or additional amino acids (e.g., poly His) placed on either terminus to create conveniently located restriction sites or termination codons or purification sequences.

A. Expression in Prokaryotes

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding site sequences, include such commonly used promoters as the beta lactamase (penicillinase) and lactose (lac) promoter systems (Chang et al., Nature 198:1056 (1977)), the tryptophan (trp) promoter system (Goeddel et al., Nucleic Acids Res. 8:4057 (1980)) and the lambda derived P L promoter and N-gene ribosome binding site (Shimatake et al., Nature 292:128 (1981)). The inclusion of selection markers in DNA vectors transfected in *E. coli* is also useful. Examples of such markers include genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using Bacillus sp. and Salmonella (Palva, et al., *Gene* 22: 229–235 (1983); Mosbach, et al., *Nature* 302: 543–545 (1983)).

B. Expression in Eukaryotes

A variety of eukaryotic expression systems such as yeast, insect cell lines, plant and mammalian cells, are known to those of skill in the art. As explained briefly below, a of the present invention can be expressed in these eukaryotic systems. In some embodiments, transformed/transfected plant cells, as discussed infra, are employed as expression systems for production of the proteins of the instant invention.

Synthesis of heterologous proteins in yeast is well known. Sherman, F., et al., *Methods in Yeast Genetics*, Cold Spring Harbor Laboratory (1982) is a well recognized work describing the various methods available to produce the protein in yeast. Suitable vectors usually have expression control sequences, such as promoters, including 3-phosphoglycerate kinase or other glycolytic enzymes, and an origin of replication, termination sequences and the like as desired. For instance, suitable vectors are described in the literature (Botstein, et al., *Gene* 8: 17–24 (1979); Broach, et al., *Gene* 8: 121–133 (1979)).

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences encoding proteins of the present invention can also be ligated to various expression vectors for use in transfecting cell cultures of, for instance, mammalian, insect, or plant origin. Illustrative of cell cultures useful for the production of the peptides are mammalian cells. Mammalian cell systems often will be in the form of monolayers of cells although mammalian cell suspensions may also be used. A number of suitable host cell lines capable of expressing intact proteins have been developed in the art, and include the HEK293, BHK21, and CHO cell lines. Expression vectors for these cells can include expression control sequences, such as an origin of replication, a promoter (e.g., the CMV promoter, a HSV tk promoter or pgk (phosphoglycerate kinase) promoter), an enhancer (Queen et al., *Immunol. Rev.* 89: 49 (1986)), and necessary processing information sites, such as rbosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas (7th edition, 1992).

Appropriate vectors for expressing proteins of the present invention in insect cells are usually derived from the SF9 baculovirus. Suitable insect cell lines include mosquito larvae, silkworm, armyworm, moth and Drosophila cell lines such as a Schneider cell line (See Schneider, *J Embryol. Exp. Morphol.* 27: 353–365 (1987).

As with yeast, when higher animal or plant host cells are employed, polyadenlyation or transcription terminator sequences are typically incorporated into the vector. An example of a terminator sequence is the polyadenlyation sequence from the bovine growth hormone gene. Sequences for accurate splicing of the transcript may also be included. An example of a splicing sequence is the VP1 intron from SV40 (Sprague, et al., *J. Virol.* 45: 773–781 (1983)). Additionally, gene sequences to control replication in the host cell may be incorporated into the vector such as those found in bovine papilloma virus type-vectors. Saveria-Campo, M., Bovine Papilloma Virus DNA a Eukaryotic Cloning Vector in DNA Cloning Vol. II a *Practical Approach*, D. M. Glover, Ed., IRL Press, Arlington, Va. pp. 213–238 (1985).

Transfection/Transformation of Cells

The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for efficient transformation/transfection may be employed.

A. Plant Transformation

The genes of the present invention can be used to transform any plant. In this manner, genetically modified plants, plant cells, plant tissue, seed, and the like can be obtained. Transformation protocols may vary depending on the type of plant cell, i.e. monocot or dicot, targeted for transformation. Suitable methods of transforming plant cells include microinjection (Crossway et al. (1986) Biotechniques 4:320–334), electroporation (Riggs et al (1986) *Proc. Natl. Acad. Sci. USA* 83:5602–5606, Agrobacterium mediated transformation (Hinchee et al. (1988) *Biotechnology* 6:915–921), direct gene transfer (Paszkowski et al (1984) *EMBO J.* 3:2717–2722), and ballistic particle acceleration (see, for example, Sanford et al. U.S. Pat. No. 4,945,050; Tomes et al "Direct DNA Transfer into Intact Plant Cells via Microprojectile Bombardment" In Gamborg and Phillips (Eds.) *Plant Cell, Tissue and Organ Culture: Fundamental Methods*, Springer-Verlag, Berlin (1995); and McCabe et al. (1988) *Biotechnology* 6:923–926). Also see, Weissinger et al. (1988) *Annual Rev. Genet.* 22:421–477; Sanford et al. (1987) *Particulate Science and Technology* 5:27–37 (onion); Christou et al. (1988) *Plant Phisiol.* 87:671–674 (soybean); McCabe et al. (1988) *Bio/Technology* 6:923–926 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes et al. "Direct DNA Transfer into Intact Plant Cells via Microprojectile Bombardment" In Gamborg and Phillips (Eds.) *Plant Cell, Tissue and Organ Culture: Fundamental Methods*. Springer-Verlag, Berlin (1995) (maize); Klein et al. (1988) *Plant Physiol.* 91:440–444 (maize) From et al. (1990) *Biotechnology* 8:833–839 (maize); Hooydaas-Van Slogteren & Hooykaas (1984) *Nature* (London) 311:763–764; Bytebier et al. (1987) *Proc. Natl. Acad. Sci. USA* 84:5345–5349 (Liliaceae); De Wet et al. (1985) In *The Experimental Manipulation of Ovule Tissues* ed. G. P. Chapman et al. pp. 197–209. Longman, N.Y. (pollen); Kaeppler et al. (1990) *Plant Cell Reports* 9:415–418; and Kaeppler et al (1992) *Theor. Appl. Genet.* 84:560–566 (whisker-mediated transformation); D'Halluin et al (1992) *Plant Cell* 4:1495–1505 (electroporation); LI et al (1993) *Plant Cell Reports* 12:250–255 and Christou and Ford (1995) *Annals of Botany* 75:745–750 (maize via *Agrobacterium tumefaciens*); all of which are herein incorporated by reference.

The cells, which have been transformed, may be grown into plants in accordance with conventional ways. See, for example, McCormick et aL. (1986) *Plant Cell Reports*, 5:81–84. These plants may then be grown, and either pollinated with the same transformed strain or different strains, and the resulting hybrid having the desired phenotypic characteristic identified. Two or more generations may be grown to ensure that the subject phenotypic characteristic is stably maintained and inherited and then seeds harvested to ensure the desired phenotype or other property has been achieved.

One of skill will recognize that after the recombinant expression cassette is stably incorporated in transgenic plants and confirmed to be operable, it can be introduced into other plants by sexual crossing. Any of a number of standard breeding techniques can be used, depending upon the species to be crossed.

In vegetatively propagated crops, mature transgenic plants can be propagated by the taking of cuttings or by tissue culture techniques to produce multiple identical plants. Selection of desirable transgenics is made and new varieties are obtained and propagated vegetatively for commercial use. In seed propagated crops, mature transgenic plants can be self crossed to produce a homozygous inbred plant. The inbred plant produces seed containing the newly introduced heterologous nucleic acid. These seeds can be grown to produce plants that would produce the selected phenotype.

Parts obtained from the regenerated plant, such as flowers, seeds, leaves, branches, fruit, and the like are included in the invention, provided that these parts comprise cells comprising the isolated nucleic acid of the present invention. Progeny and variants, and mutants of the regenerated plants are also included within the scope of the invention, provided that these parts comprise the introduced nucleic acid sequences.

A preferred embodiment is a transgenic plant that is homozygous for the added heterologous nucleic acid; i.e., a transgenic plant that contains two added nucleic acid sequences, one gene at the same locus on each chromosome of a chromosome pair. A homozygous transgenic plant can be obtained by sexually mating (selfing) a heterozygous transgenic plant that contains a single added heterologous nucleic acid, germinating some of the seed produced and analyzing the resulting plants produced for altered expression of a polynucleotide of the present invention relative to a control plant (i.e., native, non-transgenic). Back-crossing to a parental plant and out-crossing with a non- transgenic plant are also contemplated.

B Transfection of prokaryotes, Lower Eukaryotes, and Animal Cells

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextran, electroporation, biolistics, and micro-injection of the DNA directly into the cells. The transfected cells are cultured by means well known in the art. Kuchler, R. J., *Biochemical Methods in Cell Culture and Virology*, Dowden, Hutchinson and Ross, Inc. (1977).

Synthesis of Proteins

The proteins of the present invention can be constructed using non-cellular synthetic methods. Solid phase synthesis of proteins of less than about 50 amino acids in length may be accomplished by attaching the C-terminal amino acid of the sequence to an insoluble support followed by sequential addition of the remaining amino acids in the sequence. Techniques for solid phase synthesis are described by Barany and Merrifield, Solid-Phase Peptide Synthesis, pp. 3–284 in *The Peptides: Analysis, Synthesis, Biology. Vol. 2: Special Methods in Peptide Synthesis, Part A*.; Merrifield, et al., *J. Am. Chem. Soc.* 85: 2149–2156 (1963), and Stewart et al., *Solid Phase Peptide Synthesis*, 2nd ed., Pierce Chem. Co., Rockford, Ill. (1984). Proteins of greater length may be synthesized by condensation of the amino and carboxy termini of shorter fragments. Methods of forming peptide bonds by activation of a carboxy terminal end (e.g., by the use of the coupling reagent N,N'-dicycylohexylcarbodiimide)) is known to those of skill.

Purification of Proteins

The proteins of the present invention may be purified by standard techniques well known to those of skill in the art. Recombinantly produced proteins of the present invention can be directly expressed or expressed as a fuision protein. The recombinant protein is purified by a combination of cell lysis (e.g., sonication, French press) and affinity chromatography. For fusion products, subsequent digestion of the fusion protein with an appropriate proteolytic enzyme releases the desired recombinant protein.

The proteins of this invention, recombinant or synthetic, may be purified to substantial purity by standard techniques well known in the art, including selective precipitation with such substances as ammonium sulfate, column chromatography, immunopurification methods, and others. See, for instance, R. Scopes, *Protein Purification: Principles and Practice*, Springer-Verlag: N.Y. (1982); Deutscher, *Guide to Protein Purification*, Academic Press (1990). For example, antibodies may be raised to the proteins as described herein. Purification from *E. coli* can be achieved following procedures described in U.S. Pat. No. 4,511,503. The protein may then be isolated from cells expressing the protein and further purified by standard protein chemistry techniques as described herein. Detection of the expressed protein is achieved by methods known in the art and include, for example, radioimmunoassays, Western blotting techniques or immunoprecipitation.

Modulating Polypeptide Content and/or Composition

The present invention further provides a method for modulating (i.e., increasing or decreasing) endoglucanase content or composition in a plant or part thereof. Modulation can be effected by increasing or decreasing the endoglucanase content (i.e., the total amount of endoglucanase) and/or the endoglucanase composition (the ratio of various endoglucanase monomers in the plant) in a plant. The method comprises transforming a plant cell with a recombinant expression cassette comprising a polynucleotide of the present invention as described above to obtain a transformed plant cell, growing the transformed plant cell under plant forming conditions, and inducing expression of a polynucleotide of the present invention in the plant for a time sufficient to modulate endoglucanase content and/or composition in the plant or plant part.

In some embodiments, a recombinase in a plant may be modulated by altering, in vivo or in vitro, the promoter of a non-isolated endoglucanase gene to up- or down-regulate gene expression. In some embodiments, the coding regions of native endoglucanase genes can be altered via substitution, addition, insertion, or deletion to decrease activity of the encoded enzyme. See, e.g., Kmiec, U.S. Pat. No. 5,565,350; Zarling et al., PCT/US93/03868. And in nucleic acid (e.g., a vector) comprising a promoter sequence is transfected into a plant cell. Subsequently, a plant cell comprising the promoter operably linked to a polynucleotide of the present invention is selected for by means known to those of skill in the art such as, but not limited to, Southern blot, DNA sequencing, or PCR analysis using primers specific to the promoter and to the gene and detecting amplicons produced therefrom. A plant or plant part altered or modified by the foregoing embodiments is grown under plant forming conditions for a time sufficient to modulate endoglucanase content and/or composition in the plant. Plant forming conditions are well known in the art and discussed briefly, supra.

In general, content or composition is increased or decreased by at least 5%, 10%, 20%, 30%, 40%, 50%, 60%, 70%, 80%, or 90% relative to a native control plant, plant part, or cell lacking the aforementioned recombinant expression cassette. Modulation in the present invention may occur during and/or subsequent to growth of the plant to the desired stage of development. Modulating nucleic acid expression temporally and/or in particular tissues can be controlled by employing the appropriate promoter operably linked to a polynucleotide of the present invention in, for example, sense or antisense orientation as discussed in greater detail, supra. Induction of expression of a polynucleotide of the present invention can also be controlled by exogenous administration of an effective amount of inducing compound. Inducible promoters and inducing compounds which activate expression from these promoters are well known in the art. In preferred embodiments, lignification is modulated in monocots, particularly maize.

Molecular Markers

The present invention provides a method of genotyping a plant comprising a polynucleotide of the present invention. Preferably, the plant is a monocot, such as maize or sorghum. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. See, e.g., *Plant Molecular Biology: A Laboratory Manual*, Chapter 7, Clark, Ed., Springer-Verlag, Berlin (1997). For molecular marker methods, see generally, The DNA Revolution by Andrew H. Paterson 1996 (Chapter 2) in: Genome Mapping in Plants (ed. Andrew H. Paterson) by Academic Press/R. G. Landis Company, Austin, Tex., pp.7–21.

The particular method of genotyping in the present invention may employ any number of molecular marker analytic techniques such as, but not limited to, restriction fragment length polymorphisms (RFLPs). RFLPs are the product of allelic differences between DNA restriction fragments caused by nucleotide sequence variability. As is well known to those of skill in the art, RFLPs are typically detected by extraction of genomic DNA and digestion with a restriction enzyme. Generally, the resulting fragments are separated according to size and hybridized with a probe; single copy probes are preferred. Restriction fragments from homologous chromosomes are revealed. Differences in fragment size among alleles represent an RFLP. Thus, the present invention further provides a means to follow segregation of a endoglucanase gene or nucleic acid of the present invention as well as chromosomal sequences genetically linked to these genes or nucleic acids using such techniques as RFLP analysis. Linked chromosomal sequences are within 50 centiMorgans (cM), often within 40 or 30 cM, preferably within 20 or 10 cM, more preferably within 5, 3, 2, or 1 cM of a endoglucanase gene.

In the present invention, the nucleic acid probes employed for molecular marker mapping of plant nuclear genomes selectively hybridize, under selective hybridization conditions, to a gene encoding a polynucleotide of the present invention. In preferred embodiments, the probes are selected from polynucleotides of the present invention. Typically, these probes are cDNA probes or Pst I genomic clones. The length of the probes is discussed in greater detail, supra, but are typically at least 15 bases in length, more preferably at least 20, 25, 30, 35, 40, or 50 bases in length. Generally, however, the probes are less than about 1 kilobase in length. Preferably, the probes are single copy probes that hybridize to a unique locus in a haploid chromosome complement. Some exemplary restriction enzymes employed in RFLP mapping are EcoRI, EcoRv, and SstI. As used herein the term "restriction enzyme" includes reference to a composition that recognizes and, alone or in conjunction with another composition, cleaves at a specific nucleotide sequence.

The method of detecting an RFLP comprises the steps of (a) digesting genomic DNA of a plant with a restriction enzyme; (b) hybridizing a nucleic acid probe, under selective hybridization conditions, to a sequence of a polynucleotide of the present of said genomic DNA; (c) detecting therefrom a RFLP. Other methods of differentiating polymorphic (allelic) variants of polynucleotides of the present invention can be had by utilizing molecular marker techniques well known to those of skill in the art including such techniques as: 1) single stranded conformation analysis (SSCP); 2) denaturing gradient gel electrophoresis (DGGE); 3) RNase protection assays; 4) allele-specific oligonucleotides (ASOs); 5) the use of proteins which recognize nucleotide mismatches, such as the E. coli mutS protein; and 6) allele-specific PCR. Other approaches based on the detection of mismatches between the two complementary DNA strands include clamped denaturing gel electrophoresis (CDGE); heteroduplex analysis (HA); and chemical mismatch cleavage (CMC). Exemplary polymorphic variants are provided in Table I, supra. Thus, the present invention further provides a method of genotyping comprising the steps of contacting, under stringent hybridization conditions, a sample suspected of comprising a polynucleotide of the present invention with a nucleic acid probe. Generally, the sample is a plant sample; preferably, a sample suspected of comprising a maize polynucleotide of the present invention (e.g., gene, mRNA). The nucleic acid probe selectively hybridizes, under stringent conditions, to a subsequence of a polynucleotide of the present invention comprising a polymorphic marker. Selective hybridization of the nucleic acid probe to the polymorphic marker nucleic acid sequence yields a hybridization complex. Detection of the hybridization complex indicates the presence of that polymorphic marker in the sample. In preferred embodiments, the nucleic acid probe comprises a polynucleotide of the present invention.

UTR's and Codon Preference

In general, translational efficiency has been found to be regulated by specific sequence elements in the 5' non-coding or untranslated region (5' UTR) of the RNA. Positive sequence motifs include translational initiation consensus sequences (Kozak, *Nucleic Acids Res.* 15:8125 (1987)) and the 5<G>7 methyl GpppG cap structure (Drummond et al., *Nucleic Acids Res.* 13:7375 (1985)). Negative elements include stable intramolecular 5' UTR stem-loop structures (Muesing et al., *Cell* 48:691 (1987)) and AUG sequences or short open reading frames preceded by an appropriate AUG in the 5' UTR (Kozak, supra, Rao et al., *Mol. and Cell. Biol.* 8:284 (1988)). Accordingly, the present invention provides 5' and/or 3' UTR regions for modulation of translation of heterologous coding sequences.

Further, the polypeptide-encoding segments of the polynucleotides of the present invention can be modified to alter codon usage. Altered codon usage can be employed to alter translational efficiency and/or to optimize the coding sequence for expression in a desired host or to optimize the codon usage in a heterologous sequence for expression in maize. Codon usage in the coding regions of the polynucleotides of the present invention can be analyzed statistically using commercially available software packages such as "Codon Preference" available from the University of Wisconsin Genetics Computer Group (see Devereaux et al., *Nucleic Acids Res.* 12: 387–395 (1984)) or MacVector 4.1 (Eastman Kodak Co., New Haven, Conn.). Thus, the present invention provides a codon usage frequency characteristic of the coding region of at least one of the polynucleotides of the present invention. The number of polynucleotides that can be used to determine a codon usage frequency can be any integer from 1 to the number of polynucleotides of the present invention as provided herein. Optionally, the polynucleotides will be full-length sequences. An exemplary number of sequences for statistical analysis can be at least 1, 5, 10, 20, 50, or 100.

Sequence Shuffling

The present invention provides methods for sequence shuffling using polynucleotides of the present invention, and compositions resulting therefrom. Sequence shuffling is described in PCT publication Ser. No. 96/19256. See also, Zhang, J.-H., et al. *Proc. Natl. Acad. Sci. USA* 94:4504–4509 (1997) and Zhao, et al., *Nature Biotech* 16:258–261 (1998). Generally, sequence shuffling provides a means for generating libraries of polynucleotides having a desired characteristic which can be selected or screened for. Libraries of recombinant polynucleotides are generated from a population of related sequence polynucleotides which comprise sequence regions which have substantial sequence identity and can be homologously recombined in vitro or in vivo. The population of sequence-recombined polynucleotides comprises a subpopulation of polynucleotides which possess desired or advantageous characteristics and which can be selected by a suitable selection or screening method. The characteristics can be any property or attribute capable of being selected for or detected in a screening system, and may include properties of: an encoded protein, a transcriptional element, a sequence controlling transcription, RNA processing, RNA stability, chromatin conformation, translation, or other expression property of a gene or transgene, a replicative element, a protein-binding element, or the like, such as any feature which confers a selectable or detectable property. In some embodiments, the selected characteristic will be an increased $K_m$ and/or $K_{cat}$ over the wild-type protein as provided herein. In other embodiments, a protein or polynucleotide generated from sequence shuffling will have a ligand binding affinity greater than the non-shuffled wild-type polynucleotide. The increase in such properties can be at least 110%, 120%, 130%, 140% or at least 150% of the wild-type value.

Generic and Consensus Sequences

Polynucleotides and polypeptides of the present invention further include those having: (a) a generic sequence of at least two homologous polynucleotides or polypeptides, respectively, of the present invention; and, (b) a consensus sequence of at least three homologous polynucleotides or polypeptides, respectively, of the present invention. The generic sequence of the present invention comprises each species of polypeptide or polynucleotide embraced by the generic polypeptide or polynucleotide, sequence, respectively. The individual species encompassed by a polynucleotide having an amine acid or nucleic acid consensus sequence can be used to generate antibodies or produce nucleic acid probes or primers to screen for homologs in other species, genera, families, orders, classes, phylums, or kingdoms. For example, a polynucleotide having a consensus sequences from a gene family of *Zea mays* can be used to generate antibody or nucleic acid probes or primers to other Gramineae species such as wheat, rice, or sorghum. Alternatively, a polynucleotide having a consensus sequence generated from orthologous genes can be used to identify or isolate orthologs of other taxa. Typically, a polynucleotide having a consensus sequence will be at least 9, 10, 15, 20, 25, 30, or 40 amino acids in length, or 20, 30, 40, 50, 100, or 150 nucleotides in length. As those of skill in the art are aware, a conservative amino acid substitution can be used for amino acids which differ amongst aligned sequence but are from the same conservative substitution group as discussed above. Optionally, no more than 1 or 2 conservative amino acids are substituted for each 10 amino acid length of consensus sequence.

Similar sequences used for generation of a consensus or generic sequence include any number and combination of allelic variants of the same gene, orthologous, or paralogous sequences as provided herein. Optionally, similar sequences used in generating a consensus or generic sequence are identified using the BLAST algorithm's smallest sum probability (P(N)). Various suppliers of sequence-analysis software are listed in chapter 7 of *Current Protocols in Molecular Biology*, F. M. Ausubel et al., Eds., Current Protocols, a joint venture between Greene Publishing Associates, Inc. and John Wiley & Sons, Inc. (Supplement 30). A polynucleotide sequence is considered similar to a reference sequence if the smallest sum probability in a comparison of the test nucleic acid to the reference nucleic acid is less than about 0.1, more preferably less than about 0.01, or 0.001, and most preferably less than about 0.0001, or 0.00001. Similar polynucleotides can be aligned and a consensus or generic sequence generated using multiple sequence alignment software available from a number of commercial suppliers such as the Genetics Computer Group's (Madison, Wis.) PILEUP software, Vector NTI's (North Bethesda, Md.) ALIGNX, or Genecode's (Ann Arbor, Mich.) SEQUENCHER. Conveniently, default parameters of such software can be used to generate consensus or generic sequences.

Assays for Compounds that Modulate Enzymatic Activity or Expression

The present invention also provides means for identifying compounds that bind to (e.g., substrates), and/or increase or decrease (i.e., modulate) the enzymatic activity of, catalytically active polypeptides of the present invention. The method comprises contacting a polypeptide of the present invention with a compound whose ability to bind to or modulate enzyme activity is to be determined. The polypeptide employed will have at least 20%, preferably at least 30% or 40%, more preferably at least 50% or 60%, and most preferably at least 70% or 80% of the specific activity of the native, full-length endoglucanase polypeptide (e.g., enzyme). Generally, the polypeptide will be present in a range sufficient to determine the effect of the compound, typically about 1 nM to 10 $\mu$M. Likewise, the compound will be present in a concentration of from about 1 nM to 10 $\mu$M. Those of skill will understand that such factors as enzyme concentration, ligand concentrations (i.e., substrates, products, inhibitors, activators), pH, ionic strength, and temperature will be controlled so as to obtain useful kinetic data and determine the presence of absence of a compound that binds or modulates polypeptide activity. Methods of measuring enzyme kinetics is well known in the art. See, e.g., Segel, *Biochemical Calculations*, 2nd ed., John Wiley and Sons, New York (1976).

Improving Digestibility of Silage or Forage Crops

The term "silage" as used herein is intended to include all types of fermented agricultural products such as grass silage, alfalfa silage, whole plant corn silage, sorghum silage, fermented grains and grass mixtures, and the like. The present invention is particularly effective for altering digestibility of whole plant corn silage.

As used herein, "forage" means any plant stem material used to feed ruminants. Preferably, the present method is applicable to maize, sorghum, grasses and legumes. More preferably, the present method is applicable to maize.

As used herein, "grass" means any perennial or annual, cool season, seed forming plant. Grasses are sod forming, from rhizomes or by tillering.

The expression of a heterologous glucanase, such as the polynucleotides of the present invention, will increase the degradation of the glucan constituent in the cell walls of a plant. This change in cell wall composition will alter the digestibility of silage or forage crops for animals making nutrients more available and improving the nutrition of the feed. A plant transformed by an expression vector containing a constitutive or stalk-preferred promoter operably linked to a polynucleotide of the present invention will alter the composition of the cell walls of the plant thereby improving digestibility of the plant to be used for feed.

Improving Growth in a Plant

To enhance the growth rate of a plant the polynucleotides of the present invention are used to transform and express a glucanase in the plant. By increasing the expression of the glucanase in growing tissues, particularly in seedling tissues such as the coleoptile, general growth enhancement can be seen. The cell wall is the limiting factor in plant cell expansion. By altering the cell wall composition by expression of the polynucleotides of the present invention, plant cells will be allowed to expand at a faster rate. The expression of the polynucleotides can be constitutive (via a constitutive promoter), developmentally preferred (via a seedling preferred promoter) or the like, depending on the desired outcome. The substrate for the enzymes of the present invention is available in growing tissues, such as, seeds, seedlings and root tips. In non-growing tissue the substrate is lacking or minimal. Therefore growing tissue rather than non-growing tissue will see a higher enzyme activity. Expression, that is, of the polynucleotides of the present invention in the seed will enhance kernel growth rates and improve seed set.

Although the present invention has been described in some detail by way of illustration and example for purposes of clarity of understanding, it will be obvious that certain changes and modifications may be practiced within the scope of the appended claims.

EXAMPLE 1

This example describes the construction cDNA libraries.
Total RNA Isolation
Total RNA was isolated from corn tissues with TRIzol Reagent (Life Technology Inc. Gaithersburg, Md.) using a modification of the guanidine isothiocyanate/acid-phenol procedure described by Chomczynski and Sacchi (Chomczynski, P., and Sacchi, *N. Anal. Biochem.* 162, 156 (1987)). In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.
Poly(A)+ RINA Isolation
The selection of poly(A)+ RNA from total RNA was performed using PolyATact system (Promega Corporation. Madison, Wis.). In brief, biotinylated oligo(dT) primers were used to hybridize to the 3' poly(A) tails on mRNA. The hybrids were captured using streptavidin coupled to paramagnetic particles and a magnetic separation stand. The mRNA was washed at high stringent condition and eluted by RNase-free deionized water.
CDNA Library Construction
cDNA synthesis was performed and unidirectional cDNA libraries were constructed using the SuperScript Plasmid System (Life Technology Inc. Gaithersburg, Md.). The first stand of cDNA was synthesized by priming an oligo(dT) primer containing a Not I site. The reaction was catalyzed by SuperScript Reverse Transcriptase II at 45° C. The second strand of cDNA was labeled with alpha-$^{32}$P-dCTP and a portion of the reaction was analyzed by agarose gel electrophoresis to determine cDNA sizes. cDNA molecules smaller than 500 base pairs and unligated adapters were removed by Sephacryl-S400 chromatography. The selected cDNA molecules were ligated into pSPORT1 vector in between of Not I and Sal I sites.

EXAMPLE 2

This example describes cDNA sequencing and library subtraction.
Sequencing Template Preparation
Individual colonies were picked and DNA was prepared either by PCR with M13 forward primers and M13 reverse primers, or by plasmid isolation. All the cDNA clones were sequenced using M13 reverse primers.

Q-bot Subtraction Procedure cDNA libraries subjected to the subtraction procedure were plated out on 22×22 cm² agar plate at density of about 3,000 colonies per plate. The plates were incubated in a 37° C. incubator for 12–24 hours. Colonies were picked into 384-well plates by a robot colony picker, Q-bot (GENETIX Limited). These plates were incubated overnight at 37° C.

Once sufficient colonies were picked, they were pinned onto 22×22 cm² nylon membranes using Q-bot. Each membrane contained 9,216 colonies or 36,864 colonies. These membranes were placed onto agar plate with appropriate antibiotic. The plates were incubated at 37° C. for overnight.

After colonies were recovered on the second day, these filters were placed on filter paper prewetted with denaturing solution for four minutes, then were incubated on top of a boiling water bath for additional four minutes. The filters were then placed on filter paper prewetted with neutralizing solution for four minutes. After excess solution was removed by placing the filters on dry filter papers for one minute, the colony side of the filters were place into Proteinase K solution, incubated at 37° C. for 40–50 minutes. The filters were placed on dry filter papers to dry overnight. DNA was then cross-linked to nylon membrane by UV light treatment.

Colony hybridization was conducted as described by Sambrook, J., Fritsch, E. F. and Maniatis, T., in Molecular Cloning: A laboratory Manual, $2^{nd}$ Edition). The following probes were used in colony hybridization:

1. First strand cDNA from the same tissue as the library was made from to remove the most redundant clones.
2. 48–192 most redundant cDNA clones from the same library based on previous sequencing data.
3. 192 most redundant cDNA clones in the entire maize EST database.
4. A Sal-A20 oligo nucleotide: TCG ACC CAC GCG TCC GAA AAA AAA AAA MA AAA, removes clones containing a poly A tail but no cDNA.
5. cDNA clones derived from rRNA.

The image of the autoradiography was scanned into computer and the signal intensity and cold colony addresses of each colony was analyzed. Re-arraying of cold-colonies from 384 well plates to 96 well plates was conducted using Q-bot.

EXAMPLE 3

Materials and Methods

Plant material—Maize (*Zea mays* L., hybrid B37×Mol7) caryopses were allowed to imbibe for 1 day in running water at 27° C. and the germinated caryopses were sown on moist vermiculite in plastic trays (0 time). The seedlings were maintained under red light for 1 day during which time coleoptile length reached 5–7 mm. The seedlings were then placed in darkness for the subsequent days at 26° C. Coleoptiles were collected from the seedlings grown for 0–9 day after germination. The length and fresh weight of coleoptiles were measured to determine growth. The coleoptile tissues were frozen and stored at −70° C. until used for protein extractions. Some coleoptiles were used for determination of dry weight and polysaccharide content in the cell walls.

Extraction of proteins from maize coleoptile cell walls— Frozen coleoptile tissues were homogenized with 50 mM NaCl at 0° C. and the soluble cytoplasmic fraction was discarded by filtration with a nylon mesh. The insoluble materials retained in the mesh were successively washed with ice-cold 50 mM NaCl, cold acetone (−20° C.), and then with 50 mM NaCl, to aid in removal of membrane-bound cytoplasmic components. The washed cell wall was suspended in 3 M LiCl and a select group of wall associated proteins was extracted, according to methods of Huber and Nevins (1982). The salts in the extracts were removed by dialysis against 20 mM Na-acetate (pH 5.6) and the resulting protein solutions were used for the enzyme and protein assays.

The protein in the 20 mmol/L sodium-acetate/NaCl solution was concentrated by ultrafiltration (Amicon PM-10) and the concentrate was applied to a SP-Sephadex C-50 column (9 mm i.d. ×150 mm) equilibrated with 20 mmolnl sodium-acetate/NaCl. The column was eluted with the same buffer. Proteins including the major cell wall glucanases retained by the column were subsequently eluted with 500 mmon/L NaCl in 20 mmolnL sodium acetate (pH 5.4). After dialysis and concentration the active fractions were rechromatographed on SP-Sephadex (9 mm i.d.×300 mm) employing a linear gradient of NaCl (20–500 mnmol/L) in 20 mmol/L sodium acetate (pH 5.4) at a flow rate of 0.7 mL/min; the total volume was 500 mL. Separate exo- and endo-glucanase fractions were collected and dialyzed against 10 mmol/L potassium-phosphate citrate (pH 5.4) containing 200 mmol/L NaCl. The dialyzate was concentrated by ultrafiltration to reduce the volume to 2 ML and it was then subjected to Vio-Gel P-100 gel exclusion chromatography (18 mm i.d.×1,400 mm). Elution was in the presence of the same buffer containing 200 mmol/L NaCl. The fractions comprising exo- or endoglucanases were consolidated and rechromatographed on the P-100 column. The fractions in the profile identified as individual glucanases were combined and dialyzed against 20 mmol/L sodium acetate (pH 5.0). A portion of the dialyzed proteins was subjected to membrane filtration (pore size 0.45 $\mu$m) and injected onto an HPLC column (Bio-Rad TSK SP-5-PW) equilibrated with 20 mmol/L sodium acetate (pH 5.0). The column was eluted with a 30 mL linear gradient of 0 to 1 mol/: NaCl in the same buffer at a constant flow rate of 1.0 mL/min. Each peak eluted was collected and used in assays for enzyme activity and subjected to SDS-PAGE to assess purity. Exo- and endoglucanases thus purified were stored at −70° C. until use.

Assays for exo- and endoglucanase activities—Activities of exo- and endoglucanases were assayed employing β-D glucan (0.2% w/v), purified from oat bran, in the absence and presence of 100 $\mu$M $HgCl_2$, respectively. Mercury inhibits exoglucanase activity but not endoglucanase (see reference Huber and Nevins 1980 for details). Activities, expressed as glucose equivalents, were determined from the rate of release of reducing groups (Smoggy 1952). All the enzymatic assay incubations were conducted in the presence of 0.02% $NaN_3$. Protein was determined by the method of Bradford (1976).

Preparations of glucanase antibodies—Exo- and endoglucanases were purified from cell wall protein fraction of 3 days-old maize coleoptiles tissue as reported previously (Inouhe and Nevins 1991b). Exo—and endoglucanase antibodies were raised in female New Zealand rabbits upon administration of isolated proteins as reported earlier (Nevins et al. 1987, Inouhe and Nevins 1991b, Nevins 1992). The IgG in the supernatant was applied to a Protein A-Sepharose CL-4B column (Pharmacia). The IgG collected was dialyzed against 10 mM Na-phosphate buffer (pH 7.0) containing 1% NaCl at 4° C. and 0.5 ml-aliquots were stored at −70° C.

SDS-PAGE AND Western blots of cell wallproteins— Proteins extracted from coleoptile cell walls at different ages (ca. 60 μg) were heated at 98° C. for 2 min in the presence of 0.1% (w/v) SDS, 5% (v/v) 2-mercaptoethanol and 10% glycerol (Laemmli 1970). The solutions (5–10 μl) containing denatured proteins (5 μg) were applied to a 10% SDS-PAGE slab gel (0.75×100×150 mm) and subjected to 20 mA for 8–10 h at 4° C. The proteins separated on the SDS-PAGE gel were electrically transferred to a nitrocellulose paper by imposing 90 V for 45 min (Burnette 1981). The nitrocellulose paper was then treated with appropriate antibodies and then with goat anti-rabbit IgG conjugated to peroxidase. Those materials transferred to nitrocellulose were identified by staining with a Bio-Rad kit (Horseradish Peroxidase Conjugate Substrate Kit). Biotinylated SDS-PAGE standard proteins (Low Mw Range, Bio-Rad) were used as protein markers (Dellapenna et al. 1986). Preimrmune serum was used as a control for Western blots.

Evaluation of elongation of coleoptile segments under influence of JAA and antibodies—The effects of anti-glucanase antibodies on IAA-induced cell-elongation were examined in coleoptiles grown for 1 to 4 days after germination. Shoots including coleoptiles and leaves were excised at the mesocotyl nodes and the outer surface of coleoptiles were abraded longitudinally with moist carborundum (320 mesh). The abraded coleoptiles were cut into 5 mm-long segments from regions beginning 2 mm below the tip and leaves were removed. The sections were placed in 10 mM K-phosphate buffer (pH 6.5) containing 30 μM IAA and/or 200 μg/ml serum protein for a period of 2.5 h. After incubation, the length of the segments was measured with the aid of binocular microscope equipped with an ocular micrometer.

Determination of β-D-glucan content—Noncellulosic β-D-glucan content in cell walls was determined by the method of Luttenegger and Nevins (1985). After the completion of cell wall protein extraction, the insoluble wall was heated to 100° C. for 5 min in a water bath. Inactivated cell walls were treated with Porcine pancreatic α-amylase (Sigma Type I-A) for 12 h at 37° C. and then washed with distilled water. The cell walls were then incubated for 12 h at 37° C. with a β-D-glucanase purified from Novo Ban 120 L (Novo Industri A/S. Copenhagen, Denmark) (Kato and Nevins 1984). Total sugars released were determined by the phenol sulfuric acid method (Dubois et al. 1956) and expressed as glucose equivalents.

Deglycosylation of exo- and endoglucanases—Deglycosylation of exo- and endoglucanases was performed using Glycofree Deglycosylation Kit (Oxford GlycoSystem Inc.) according to the instructions. Sixty μg of each of the proteins each was used for the reaction. Deglycosylated proteins were dialyzed against distilled water and analyzed on 12.5 or 10.0% gel SDS-PAGE followed by transfer to nitrocellulose for Western blots.

IEF electrophoresis of glucanases—Polyacrylamide gel isoelectric focusing of exo- and endoglucanase polypeptides was conducted using a gel (5 mm i.d. ×120 mm length) containing 5% polyacrylainide and 4.4% Ampholine (pH 3.5–10, Pharmacia). Anode and cathode solutions were 20 mmol/L $H_3PO_4$ and 1 mol/L NaOH respectively. After proteins (10 μg) were loaded, the gel was maintained at 4° C. for 3 hours and resolution mediated under the influence of 260 V. An IEF calibration kit (Range pH 3–10, Pharmacia) was used for pI markers. After electrophoresis, most gels were stained with Coomassie Brilliant Blue R-250 to detect protein bands, and some were sliced into 2 mm-thick disks and placed in distilled water to establish the pH gradient.

Molecular weight determination of glucanases under non-denatured conditions—Purified native glucanases (12 μg) were applied onto a GPC column (Superdex 200HR 10/30, Pharmacia) coupled to FPLC system (Pharmacia). The column was eluted with 20 mmol/L sodium phosphate buffer (pH 6.0) containing 200 mmol/L NaCl at a flow rate of 0.2 mL/min. A Bio-Rad set of standard proteins was used for molecular weight calibration.

Determination of N-terminal amino-acid glucanase sequences—$C_{18}$-reverse phase chromatography using 0–500 mmol/L acetonitril gradient in 0.1% trifluoroacetic acid to remove minor impurities. Proteins (ca. 1 nmole) from the exo- and endoglucanase fractions were blotted on PVDF membrane using ProSpin (Applied Biosystems) and subjected to an automated Edman degradation sequencer (Applied Biosystem, Model 477A).

Purification of exo- and endoglucanases from maize coleoptile cell walls—Cell wall glucanases extracted from maize coleoptile tissues have been partially characterized in previous studies (Huber and Nevins, 1982; Hatfield and Nevins, 1986; Inouhe and Nevins, 1991b). Therefore the initial steps in the purification of exo- and endoglucanases for the present experiments were carried out largely according to existing procedures. Exo- and endoglucanase activities were effectively separated by SP-Sephadex C-50 chromatography. The two active fractions were then subjected to Bio-Gel P-100 chromatography to separate the enzymes from contaminating proteins with different molecular weights. The elution profiles for the exo- and endoglucanses were similar to those achieved previously with a Bio-Gel P-150 column (Inouhe and Nevins 1991b), but this media is no longer available from the manufacturer. And while rechromatography of the enzyme fractions with P-150 column had been sufficient to allow advancement to subsequent steps, the performance of P-100 was less effective in separation than P-150 (Inouhe and Nevins, 1991b). Therefore for these studies we added an additional HPLC step with a cation exchange column. Under the prescribed conditions, the exoglucanase eluted at a retention time of 21.9 min and the endoglucanase at 22.1 min. When the major glucanase fractions were subjected to SDS-PAGE, the exoglucanase resolved as a single band at ca. 73 kDa and the endoglucanases as double bands at ca. 33 and 34 kDa, as reported previously (Inouhe and Nevins, 1991b). The average molecular weights (±SE) of those polypeptides after repeated determinations were 73.5±0.3, 32.9±0.4 and 34.3±0.4 kDa, respectively (n=8).

Molecular weights and charge of native glucanase—Purified glucanases were subjected to chromatography with Superdex 200HR to estimate apparent molecular weights under native conditions. Exoglucanase eluted at 66.6 min and endoglucanase at 73.0. Based on the calibration of the column with standard proteins, the indicated molecular weight of the exoglucanase was 55±2 kDa (n=3) and that of the endoglucanase was 29+3 kDa. IEF electrophoresis of the enzymes on a native rod gel with a pH gradient 3–10 demonstrated that the exoglucanase is predominately a single polypeptide with a pI 7.2 and the endoglucanase was resolved as two polypeptides with pI values of 7.8 and 7.3.

Extent of glycosylation—To determine the extent to which the glucanases were glycosylated, both exo- and endoglucanases were deglycosylated employing a standard kit and the products of the reaction subjected to SDS-PAGE. When analyzed on a 12.5% gel, the migration of the two major endoglucanase isozymes (34.3 and 32.9 kDa) was no longer apparent and both components were found as a single band with a mass of 30.0 kDa. The migration of the exoglucanase was not affected by deglycosylation when subjected to a 12.5% SDS-PAGE. However, when the exoglucanase was analyzed on a 10% gel, a significant decrease in molecular weight to ca. 68.5 kDa was observed. These results are consistent with the suggestion that both glucanases are glycoproteins and differ in the extent or arrangement of glycan substituents.

Structural aspects of antibody binding—Polyclonal antibodies raised in response to injection of the purified native glucanases into rabbits were used to evaluate immunological identity of the polypeptide structures. Western blots revealed that the polyclonal antibodies recognized only the corresponding antigen glucanases, and no cross-reactions were observed. The results suggest that the exo- and endoglucanases have immunologically distinct polypeptide sequences and glycan structures. Furthermore, both antibodies were able to recognize the polypeptide portions of the enzymes even after sugar moieties had been removed by deglycosylation. In addition, antibodies, generated in response to the injection of β-(1,3)(1,4)-glucan into rabbits did not cross react with the exo- and endoglucanases. The results provided evidence that the polypeptide structures of exo- and endoglucanases were substantially different and that the major determinants for antibody recognition are based on polypeptide motifs. A preimmune serum used as a control did not react to the glucanases or other cell wall proteins of maize coleoptiles.

Glucanase N-terminal amino-acid sequences—Native exo- and endoglucanases isolated by HPLC equipped with a reverse phase column, were subjected to analysis by an automated gas-phase protein sequencer (model 470A, Applied Biosystems) to determine the amino-terminal sequence. As shown in FIG. 7, 23 residues for the exoglucanase and 30 residues for the endoglucanase were readable. No homologous sequences were found between exo- and endoglucanase polypeptides. Exoglucanase was enriched in basic amino acid residues (3K, 2R) while the endoglucanase was not (1R, 1H). The latter might be expected to contain basic amino acids in the internal sequence.

Protein purification and sequence; gene sequence—Purification and partial sequencing of the maize coleoptile endo-1,3;1,4-beta glucanase enzyme (Inouhe 1998b) suggested that this enzyme was distinct from the superfamily of 1,3-beta-glucanases and 1,3;1,4-beta-glucanases, which contains the endo-1,3;1,4-beta-glucanases studied previously in seedling caryopsis (Simmons 1994). The DNA sequence deduced from this peptide sequence was used to search in the maize EST proprietary database at Pioneer Hi-Bred. One cDNA clone, which matched the coleoptile endoglucanase sequence, was completely sequenced.

Analysis of this maize coleoptile endoglucanase DNA sequence via BLAST searches in the GenBank database showed no similarity to any plant endoglucanase gene studied previously. While recent discoveries of divergent new genes in glycosyl hydrolase family 17 (Rodriguez 1997, Romero 1998) have added to the complexity of this gene family (Li 1996), there remain a set of conserved sequences that are shared by all members of the gene family. The coleoptile endoglucanase described here clearly represents a new and distinct gene family because it completely lacks the conserved sequences found in family 17.

The predicted properties of the peptide encoded by this cDNA correlate well with the properties of the enzyme purified from maize coleoptiles (Inouhe 1998b, Inouhe 1991 b, Hatfield 1986) (Table 1). A hydrophobic signal peptide is involved in the secretion of this enzyme into the cell wall where its substrate is located. Small discrepancies in the molecular mass and pI of the mature peptide may result from the glycosylation of the endoglucanase. Sequence information appears in Table 2.

TABLE 1

Peptide properties of maize coleoptile endoglucanase.

|  | Deduced from DNA sequence | Enzyme purified from coleoptiles |
|---|---|---|
| Signal peptide Molecular mass | 2.1 kD |  |
| Mature peptide Molecular mass | 31 kD | 33–35 kD |
| pI | 6.9 | 7.3–7.8 |

Table 2. Nucleotide (cDNA, SEQ ID NO: 1) and protein sequence for endo 1,3;1,4-β-glucanase (SEQ ID NO: 2).

TABLE 2

Nucleotide (cDNA, SEQ ID NO: 1) and protein sequence for endo 1,3;1,4-β-glucanase (SEQ ID NO: 2).

\>CXMAE63R, cDNA beta-glucanase, 1002 bp minus polyA..

```
AGCCCACAACCATTATTCTTATTCCACTGCATCAGGTCCAAGTCCAACTCTCCAAGCGGCAAGCGC
CATGCCTTCTTCCGCGCAGGTTCTGCTCTGCCTCGCCGCCGTGCTGGCGGCGGCGGCCACCAC
CGCCGAGGCGCACTCGCAGTGCCTGGACAACCCGCCGGACCGGTCCATCCACGGCCGCCAGCTGGC
CGAGGCCGGCGAGGTCGTCCACGACCTCCCCGGTGGCCTCAGGGCCTACGTCAGCGGCGCCGCGAG
CTCGAGCCGCGCCGTCGTCCTCGCCTCCGACGTCTTCGGGTACGAGGCGCCATTGCTCAGACAGAT
AGTAGACAAGGTTGCAAAGGCAGGGTACTTCGTCGTCGTGCCCGATTTCTTGAAGGGAGACTACTT
AGACGACAAGAAAAACTTTACAGAATGGCTCGAGGCTCACTCTCCGGTGAAAGCTGCGGAAGACGC
TAAGCCACTGTTCGCCGCTTTGAAGAAGGAAGGGAAGTCCGTCGCGGTGGGAGGCTACTGCTGGGG
AGGGAAGCTGAGCGTGGAGGTGGGGAAGACCAGCGACGTCAAAGCTGTGTGCCTTTCGCACCCGTA
CAGCGTCACTGCCGACGACATGAAAGAGGTGAAATGGCCGATCGAGATCCTGGGGGCCCAGAACGA
CACGACCACGCCGCCGAAAGAAGTGTACCGGTTCGTGCATGTGCTGCGTGAAAGACACGAGGTTCC
CTTTCGCCGTCAAGACCGCAGAGACGGCCCTCGCCTACATGGTCAGCTGGTTCAACAAGCACCTCA
ACTGAATGAAGCCTGCACTGCACCCACCAGACTGAATTCAATAAACCACAGCAGTGCTGTGATATT
TTGTTTCGATTCGTGGCTCCCCAGATTGATTTTCATGGCTACGACCTCTTCTACTACTGTAATTTC
CCTCATTTTTTTTGTCTCTATGTATTTCTTTTCTTTTCTTTTTGCTTTTTTATGATCGCAATAAAG
TTCAGTAGGGTAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAA
MPSSAQVLLCLAAVLAAAAATTAEAHSQCLDNPPDRSIHGRQLAEAGEVVHDLPGGLRAYVSGAASSSR
```

TABLE 2-continued

Nucleotide (cDNA, SEQ ID NO: 1) and protein sequence for endo
1,3;1,4-β-glucanase (SEQ ID NO: 2).

>CXMAE63R, cDNA beta-glucanase, 1002 bp minus polyA..

AVVLASDVFGYEAPLLRQIVDKVAKAGYFVVVPDFLKGDYLDDKKNFTEWLEAHSPVKAAEDAKPLFAA
LKKEGKSVAVGGYCWGGKLSVEVGKTSDVKAVCLSHPYSVTADDMKEVKWPIEILGAQNDTTTPPKEVY
RFVHVLRERHEVPFRRQDRRDGPRLHGQLVQQAPQLNEACTAPTRLNSINHSSAVIFCFDSWLPRLIFM
ATTSSTTVISLIFFVSMYFFSFLFAFL

RESULTS

Growth of maize coleoptile and changes in glucan content in the cell wall—Maize seedlings were grown for a total 9 days after germination and length and fresh weight of coleoptiles were measured at one day intervals. In general, maize coleoptiles continued to elongate until about day 5, and a similar pattern was observed for increases in the fresh weights. The maximum rate of increase in both length and fresh weight of coleoptiles occurred at day 3. Coleoptile growth (elongation) ceased on day 5, when extrusion of leaves occurred. The dry weight of coleoptile increased in parallel with the fresh weight until day 5, then a net decrease in dry weight was observed. These results suggest that substantial degradation and dry matter mobilization of coleoptiles occurs after day 5.

The non-cellulosic glucan content in intact maize coleoptile rapidly increased to a maximum level (400 μg/.coleoptile) by day 4 and thereafter decreased. The maximum rate of glucan accumulation per coleoptile was ascertained to occur on about day 2, which precedes the stage for maximum growth rate of coleoptile by about 1 d, an observation consistent with that reported earlier (Luttenegger and Nevins 1985). When expressed on a cell wall dry weight basis, the level of glucan was highest on day 2 and then gradually decreased through day 9.

Glucanase activities in protein fractions extracted from maize coleoptile cell walls as a function of development—Changes in cell wall proteins extracted with 3 M LiCl during coleoptile development were observed. The total content of protein in the 3 M LiCl extract of coleoptile cell walls increased for first 2–3 days then rapidly decreased, suggesting that cell wall protein is governed not only by synthetic activities but also by rapid turnover. These experiments also reveal that exo- and endoglucanase activities in the cell wall protein fractions were augmented gradually during development. Exoglucanase activity increased after germination, to a maximum level by day 5, and then that level was maintained or only slightly decreased. Endoglucanase activity was not detected on day 1, but thereafter increased significantly up to days 5–6. This pattern was confirmed by subsequent viscometric assay using oat bran glucan as substrate. The observed changes in activities of both exo- and endo- glucanases correspond to changes in autolytic activities of maize coleoptile cell walls during coleoptile growth (Inouhe and Nevins 1997a).

Changes in the glucanase polypeptide components in maize coleoptile cell walls—The first possibility to be considered in reconciling the metabolism of glucan in the cell wall with a mechanism would be an activity change in glucanases based on enhanced syntheses and incorporation during cell wall development. To confirm the specific polypeptide levels as a function of development, we subjected equal amounts of cell wall protein (5 μg) prepared on each day to SDS-PAGE and compared the densities of protein bands by specific conjugation to exo- or endoglucanase-antibodies on Western blots. A protein band (74 kDa) which conjugated with anti-exoglucanase antibodies appeared on day 1, and its density increased until about day 5. On the other hand, the protein bands (33 and 31.5 kDa) corresponding to the major and minor isoforms of endoglucanase were detected only after day 2 and thereafter increased until day 6. These changes in protein bands were proportional to activities in assays for respective glucanase.

Effect of auxin on the glucanase contents in maize coleoptile cell walls—The administration of auxin has been reported to mediate a substantial decline in net glucan content in cell walls of coleoptile segments (Loescher and Nevins 1972). Auxin, therefore, might be expected to induce synthesis or activate cell wall glucanases. However, we found that auxin treatment of segments had little effect on the densities of protein bands representing exo- and endoglucanases extracted from coleoptile cell walls. The results suggest that the response to auxin in bioassays with isolated segments does not occur by de novo syntheses of cell wall glucanases as a means for augmentation of wall glucan metabolism.

The effectiveness of glucanase antibodies for inhibiting cell elongation of segments derived from coleoptiles of different ages—Exo- and endoglucanase antibodies significantly suppress auxin-induced cell elongation of 3 day-old maize coleoptile segments, by virtue of their suppression of glucan metabolisms (Inouhe and Nevins 1991b). We find that growth inhibition caused by antibodies is similar with segments taken from 3 days-old coleoptiles irrespective of the distance from the apex, 3 to 13 mm vs 15 to 25 mm (unpublished data). Effects of exo- and endoglucanase antibodies on IAA-induced cell elongation of coleoptile segments were examined in segments prepared at different stages (days 1–4) to elucidate the significance of glucanases throughout development. Exo- and endoglucanase antibodies strongly inhibited IAA-induced cell elongation of coleoptile segments on days 3—4, when the rate of elongation is maximum in coleoptiles. Such inhibition was not apparent on day 1. These results suggest that cell wall glucanases may exercise their primary function in controlling coleoptile growth after an initial developmental phase. Even in the absence of external LIA, 1 day-old coleoptile segments exhibited substantial cell elongation, however such elongation was rather insensitive to exo- or endoglucanase antibodies. Since the length of the excised segments was the same in all bioassays, the contribution to overall coleoptile growth was less at 1 day because the one 5 mm segment at that stage constituted essentially the entire coleoptile. At later sampling times the overall growth is greater because of the combined contribution of a more extended coleoptile unit.

DISCUSSION

Glucanases have been implicated in the sequence of events leading to cell elongation and growth in cereals. Because of that putative physiological role we have sought to describe the properties of the specific exo- and endoglucanases purified from the maize coleoptile cell wall. Based on these results we can conclude that features shared in common by these proteins include the recognition that they are (1) basic in nature, (2) glycoproteins, and (3) antigenic. Previous reports on these enzymes served to characterize the additional parameters that reflect on homology viz. (4) inonic binding to the cell wall matrix, (5) specificity for the cereal β-(1,3)(1,4)-glucan as a substrate, and (6) a shared role in mediating autohydrolytic dissociation of wall components (Huber and Nevins, 1979, 1982; Hatfield and Nevins, 1986; Inouhe and Nevins, 1991b). Collectively these parameters support the concept that the enzymes are related in terms of metabolic and biological function.

With a detailed analysis of comparative features of exo- and endo- glucanases one can focus on distinctive characteristics. First, the N-terminal sequences of the enzyme are quite different. In addition, antibodies specific for the exoglucanase did not cross react with the endoglucanase and those of the endoglucanase did not react with the exoglucanase. Based on these immunological probes it would appear that there is no support for the contention that the enzymes are derivatives of a single gene.

While in the previous study, we found that excessively high concentrations of exoglucanase did show marginal affinity for the endoglucanase antibodies, excess endoglucanase did not react to exoglucanase antibodies (Inouhe and Nevins, 1991b). Earlier we tentatively proposed that the exoglucanase might be a modified form of the endoglucanase perhaps resulting from subunit association and there might be some common genomic origin (Inouhe and Nevins, 1991 b). This hypothesis is not sustained by the current results.

One of the confounding observations in previous studies was the consistent appearance of two bands with molecular weights of 34.3 and 32.9 kDa representing the purified endoglucanase on SDS-PAGE. Both bands cross reacted with the endoglucanase antibody. This observation can now be attributed to differences in glycosylation of otherwise indistinguishable polypeptides. Deglycosylation of the endoglucanase isozymes resulted in convergence into a single band at 30.0 kDa. The result suggests that the endoglucanase polypeptides are identical and that the formation of isozymes is a consequence of the extent of glycosylation. Judging from the density in the staining of the polypeptide bands, the 34.3 and 32.9 Kda endoglucanase isozymes appear to correspond to the pI 7.8 and 7.3 polypeptides on IEF-PAGE pattern, respectively. If this is the case, the expression of surface charges in the two peptides might be a consequence of glycosylation. The significance of endoglucanase glycosylation should be the objective of further study. Nevertheless it is likely that peptides, translated from the same gene, were differentially glycosylated during processing and secretion or modification may have occurred after deposition into the wall matrix. Since there is precision in the extent of glycosylation in the formation of the two isozymes one must consider the possibility that the two distinctive endoglucanases isozymes might have physiological roles.

A number of glucanases from diverse plant origins bind to concanavalin A (Hoson and Masuda, 1995) suggesting that they are glycoproteins with glucose or mannose residues as glycosyl components. This general feature of glucanases implies that the exo- and endoglucanases characterized here might be analogous. Further characterization of the glycosyl constituents will address the nature of the sugar constituents. The fact that in other cereal species, treatment of coleoptiles with con-A in the presence of auxin suppresses elongation implies that the lectin binds to glucanases in vivo thereby effectively disarming a catalytic role in mediating wall loosening (Hoson and Masuda, 1995). To date however, this mechanism for growth suppression by Con-A is based on speculation. More related to the current studies was an evaluation of glucan antibody cross reaction with the exo- or endoglucanase in Western blots. No binding was observed thereby suggesting that the glycosyl residues of exo- and endoglucanases are not related to the glucan nor are there remnants of the wall matrix glucan substrate that remain attached to the peptide.

Fincher and co-workers have identified numerous glucanase genes from barley and have demonstrated spatial and temporal expression in embryonic tissues (Mundy and Fincher, 1986; Stuart et al., 1986; Slakeski and Fincher, 1992a, b; Hoj and Fincher, 1995). They have also shown an absence of expression of glucanase genes in coleoptile tissues by Northern analysis using their glucanase DNA probes. In the results reported here we demonstrate that the maize coleoptile exoglucanase isolated from cell walls has a high homology with the exo-β 1,3-glucanase they described from 8 day old barley grains (Hrmova et al., 1996), however the endoglucanase bears little resemblance to the structural sequence of described enzymes. Thus we conclude that the gene encoding the maize exoglucanase has a conserved structural nature which it shares with other plants but the maize wall endoglucanase appears not to be included in "glucanase super gene families". A complete reading of the internal structure of the maize wall endoglucanase will provide definitive answers for that intriguing possibility that it is a unique enzyme.

Finally, we reported maize wall glucanases are glycoproteins and that the surface charges are likely to be due to amino-acid and glycosyl residues of polypeptide. Both the polypeptide and glycan moieties represent possible sites for interaction of the protein with the cell wall polysaccharides and other glycoproteins, irrespective of whether the binding is covalent or non covalent. Hence not only does it appear that a change in glucanase levels is mediated by gene expression in response to hormones but also changes in the status of the enzymes in the cell walls with respect to other constituents are likely to influence effective expression of pertinent activities within the compartment (Inouhe and Nevins, 1997, 1998).

It was observed that exo- and endoglucanase activities in coleoptile cell walls of intact maize seedlings increased 1 or 2 days after emergence of the coleoptile. The density of protein bands corresponding to exo- and endoglucanases also rapidly increased with good correspondence with changes in respective activities. Based on these results we conclude that both the exo- and endoglucanases are expressed in maize coleoptile cell walls as a function of development presumably governed by continuous exposure of auxin or as a response to some other regulatory factors, While the appearance of exoglucanase proceeded that of the endoglucanase, the physiological significance of the sequence is not clear.

Specific activities and concentrations of exo- and endoglucanases in the extracted cell wall proteins increased after imbibition and continued throughout the 5 days of most rapid coleoptile growth. The close relationship of the two glucanases throughout development suggests that the enzymic activities reflect protein concentrations in the cell walls, and thus, are interpreted as in vitro activities expressed by de novo protein syntheses. However, this interpretation during the early stages of coleoptile development may not be appropriate after day 3. The total amount of cell wall protein per coleoptile increased for at least the initial 3 days but thereafter the amount of protein per coleoptile tended to markedly decrease. This suggests that the cell wall proteins are subjected to turnover or liberation from cell walls during the later growth stages. Secondly, the total activity (per coleoptile) of exo- and endoglucanases may be calculated by determining the product of their specific activities (activity/h/μg protein) and total cell wall protein contents (μg/coleoptile). The calculated values for total activities for exo- and endoglucanases increased up to 6.7–7.2 and 1.3–1.6 μg glucose/h/coleoptile until age 3 and 4 d, respectively, but the values remained rather constant thereafter. Similar patterns can be expected for changes in total glucanase protein per coleoptile. While in this study we did not attempt to precisely determine the protein band densities, there is little basis to expect any significant discrepancy in the relationship between activity and polypeptide abundance. These observations suggest that the accumulation of exo- and endoglucanases and other major proteins in maize coleoptile cell walls appears to be complete within 3 or 4 days after imbibition.

Fincher and co-workers have identified many glucanase genes from barley and demonstrated a spatial and temporal expression in the embryonic tissues and specific parts of the seedlings (Mundy and Fincher 1986, Stuart et al. 1986, Slakeski and Fincher 1992a, b). They have also shown an absence of expression of glucanase genes in coleoptile tissues by northern analyses using their glucanase DNA probes. In the present study, we clearly demonstrated that maize coleoptiles contain high exo-and endoglucanase activities in the cell walls, consistent with previous reports (Huber and Nevins 1981 a, Hatfield and Nevins 1986, Inouhe and Nevins 1991b), and the levels of these enzymes are augmented during coleoptile development. While there is a possibility that maize coleoptile glucanases have structures which would not be revealed by barley glucanase probes, that possibility seems unlikely. Alternatively, consideration should be given to the possible difference in the expression sequence of respective glucanase genes between related taxa. Precise studies on glucanase structural homology and mRNA syntheses for maize coleoptile glucanases will be required to confirm this contingency.

Auxin generally promotes a net decrease in the non-cellulosic glucan content in cereal coleoptile cell walls (Loescher and Nevins 1972, Sakurai et al. 1978a, Zarra and Masuda 1979b, Inouhe and Nevins 1991a). Moreover auxin-treated maize coleoptile segments retain an enhanced auto-hydrolytic activity in cell walls even after they are prepared from the segments (Inouhe and Nevins 1991 a). These observations have led to the suggestion that auxin stimulates glucan metabolism by intricate regulation of cell wall glu-canases. Auxin control of glucanases activity may be explained by either enhanced activities of preexisting enzymes or through enhanced syntheses of the enzymes or even some combination of the two possibilities. In the present experiments, we confirmed that auxin had little direct effect on the amount of extracted exo- and endoglu-canses of 3 day-old coleoptile cell walls (FIG. 4). This evidence implies that auxin may not directly promote the new syntheses of glucanases as a part of the response. In addition, auxin has been linked to acidification of the cell wall compartment thereby lowering the pH to around pH 5 (Hager et al. 1971, Cleland 1971, 1992). The acid growth hypothesis typically considers that the basis of growth promotion results from a decreased pH which favors certain cell wall hydrolytic enzymes, hence activities of preexisting enzymes are enhanced. Such a pH change in situ might be a reasonable way for auxin to stimulate glucanases which are more active at acidic pH. However, treatment of segments with acidic buffers (pH 4–4.5) alone, does not stimulate in vivo glucan degradation typically associated with auxin responses (Loescher and Nevins 1973, Sakurai and Masuda 1977) nor does lower pH enhance wall glucan autolysis (Inouhe and Nevins 1991a). Change in the cell wall autolysis induced by auxin is maintained after extraction and is independent of the pH (4.0 to 7.0) in in vitro reaction buffers for at least 2–4 h (Inouhe et al. 1991 a). Hence auxin enhances the activity by a mechanism other than wall acidification. There are numerous reports of auxin stimulation of syntheses of certain proteins (O'Neill and Scott 1987, Edelmann and Kutschera 1993) as well as polysaccharides which are then incorporated into wall (Inouhe et al. 1987, Yamamoto et al. 1988). Certainly expression of many proteins, including glucanases would be expected for a multitude of other events occurring in coleoptile cell walls. The relationship between these auxin mediated events and glucanase activity need to be resolved in order to identify putative regulatory substances or structural elements which mediate the glucanase-glucan interactions in cell walls under influence of auxin. One putative regclatory protein (AWP) was separated from maize coleoptile cell walls (Inouhe and Nevins 1997b).

Polyclonal antibodies raised against cell wall proteins have been used to investigate the role of selected cell wall components in extension growth (Huber and Nevins 1981b, Hatfield and Nevins 1988, Hoson and Nevins 1989b, Nevins 1992). Antibodies, obtained from rabbits after injection with maize coleoptile wall protein fractions, strongly inhibit elongation of maize coleoptile segments and suppress wall β-D-glucan autolysis (Huber and Nevins 1981). Antibodies raised in response to the administration of the structurally homologous Avena (1,3): (1,4)- β-D glucans and those prepared against exo- and/or endo-glucanases purified from maize cell walls also significantly inhibit IAA-induced cell elongation and wall autohydrolysis of maize coleoptiles (Hoson and Nevins 1989a, Inouhe and Nevins 1991b). The data taken together are consistent with the concept that an important glucanase-mediated event is responsible for cell wall glucan-metabolism in auxin-induced cell elongation in coleoptile segments. Now, studies on the effect of antibodies have been extended to include tissues of different ages including those in which glucanases were just beginning to become expressed. Most interesting was the observation that the exo- and endoglucanase antibodies had little inhibitory effects in IAA-induced cell elongation of coleoptile segments on day 1. The simple explanation for this observation may be that enzymes targeted by the glucanase antibodies are not functional in growth at earlier stages of coleoptile growth.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The invention has been described with reference to various specific and preferred embodiments and techniques. However, it should be understood that many variations and modifications may be made while remaining within the spirit and scope of the invention.

REFERENCES

Bradford, M. M. (1976) A rapid and sensitive method for the quantitation of microgram quantities of protein utilizing the principle of protein dye binding. *Anal. Biochem.* 72: 248–254.

Burnette, W. N. (1981) "Western blotting": Electrophoretic transfer of proteins from sodium dodecyl sulfate-polyacrylamide gels to unmodified nitrocellulose and radioactive protein. A. *Anal. Biochem.* 112: 195–203.

Cleland, R. E. (1971) Cell wall extension. *Annu. Rev. Plant Physiol.* 22: 197–222.

Cleland, R. E. (1992) Auxin-induced growth of Avena coleoptile involves two mechanisms with different pH optima. *Plant Physiol.* 99: 1556–1561.

Dellapenna, D., Christofferson, R. E. and Bennett, A. B. (1986) Biotinylated proteins as molecular weight standards on Western blots. *Anal. Biochem.* 152: 329–332.

Dopico, B., Nicolas, G. and Labrador, E. (1990) Characterization of a cell wall β-galactosidase of Cicer arietinum epicotyls involved in cell wall autolysis. *Physiol. Plant.* 80: 629–635.

Dubois, M., Gilles, K. A., Hamilton, J. K., Rebers, P. A. and Smith, F. (1956) Colorimetric method for determination of sugars and related substances. *Anal Chem.* 28: 350–356.

Edelmaun, H. G. and Kutschera, U. (1993) Rapid auxin-induced enhancement of protein biosynthesis inryecoleoptiles. *J Plant Physiol.* 142: 343–346.

Greve, L. C. and Ordin, L. (1977) Isolation and purification of an α-mannosidase from coleoptiles of Avena sativa. *Plant Physiol.* 60: 478–481.

Hager, A., Menzel, H. and Krauss, A. (1971) Versuche and Hypothese zur Primarwirkung des Auxins beim Streckungswachstum. *Planta* 100: 47–75.

Hatfield, R. and Nevins, D. J. (1986) Purification and properties of an endoglucanase isolated from the cell walls of Zea mays seedling cell walls. *Carbohydr. Res.* 148: 265–278.

Hatfield, R. and Nevins, D. J. (1987) Hydrolytic activity and substrate specificity of an endoglucanase from Zea mays seedling cell walls. *Plant Physiol.* 83: 203–207.

Hatfield, R. and Nevins, D. J. (1988) Plant cell wall proteins: Plant cell wall proteins: partial characterization of maize wall proteins with putative roles in auxin-induced growth. *Plant Cell Physiol.* 29: 713–720.

Hayashi, T. and Ohsumi, C. (1994) Endo-1,4-β-glucanase in the cell wall of stems of auxin-treated pea seedlings. *Plant Cell Physiol.* 35: 419–424.

Hoj, P. B. and Fincher, G. B. (1995) Molecular evolution of plant β-glucan endohydrolase. *Plant J.* 7: 367–379.

Hoson, T. (1993) Regulation of polysaccharide breakdown during auxin-induced cell wall loosening. *J. Plant Res.* 106: 369–381.

Hoson, T. and Masuda, Y. (1995) Concanavalin A inhibits auxin-induced elongation and breakdown of (1–73), (1–74) β-D-glucans in segments of nice coleoptiles. *Plant Cell Physiol.* 36: 517–523.

Hoson, T. and Nevins, D. J. (1989a) β-D-glucan antibodies inhibit auxin-induced cell elongation and changes in the cell wall of Zea coleoptile segments. *Plant Physiol.* 90: 1353–1358.

Hoson, T. and Nevins, D. J. (1989b) Effect of anti-wall protein antibodies on auxin-induced elongation, cell wall loosening, and β-D-glucan degradation in maize coleoptile segments. *Physiol. Plant.* 77: 208–215.

Huber, D. J. and Nevins, D. J. (1979) Autolysis of cell wall β-D-glucan in corn coleoptiles. *Plant Cell Physiol.* 20: 201–212.

Huber, D. J. and Nevins, D. J. (1980) β-D-Glucan hydrolase activity in Zea coleoptile cell walls. *Plant Physiol.* 65: 768–773.

Huber, D. J. and Nevins, D. J. (1981a) Partial purification of endo- and exo-β-D-glucanase enzymes from Zea mays L. seedlings and their involvement in cell-wall autohydrolysis. *Planta* 151: 206–214.

Huber, D. J. and Nevins, D. J. (1981b) Wall-protein antibodies as inhibitors of growth and autolytic reactions of isolated cell wall. *Physiol. Plant.* 53: 533–539.

Huber, D. J. and Nevins, D. J. (1982) Exoglucanases from Zea mays L. seedlings: their role in β-D-glucan hydrolysis and their potential role in extension growth. *Planta* 155: 467–472.

Inouhe, M., Yamamoto, R. and Masuda, Y. (1987) UDP-Glucose level as a limiting factor for IAA-induced cell elongation in Avena coleoptile segments. *Physiol. Plant.* 69: 49–54.

Inouhe, M. and Nevins, D. J. (1991a) Auxi-n-enhanced glucan autohydrolysis in maize coleoptile cell wall. *Plant Physiol.* 96: 285–290.

Inouhe, M. and Nevins, D. J. (1991b) Inhibition of auxin-induced cell elongation of maize coleoptiles by antibodies specific for cell wall glucanases. *Plant Physiol.* 96: 426–431.

Inouhe, M. and Nevins, D. J. (1997a) Changes in the autolytic activities of maize coleoptile cell walls during coleoptile growth. *Plant Cell Physiol.* 38: 161–167.

Inouhe, M. and Nevins, D. J. (1997b) Regulation of cell wall glucanase activities by non-enzymic proteins in maize coleoptiles. *Int. J. Biol. Macromol.* 21: 15–20.

Inouhe, M., Hayashi, K., and Nevins, D J (1998a) Polypeptide characteristics and immunological properties of exo- and endoglucanases purified from maize coleoptile cell walls. (in press)

Inouhe, M., and Nevins DJ (1998b) Changes in the activities and polypeptide levels of exo- and endoglucanases in cell walls during developmental growth of Zea mays coleoptiles. *Plant Cell Physiol* (in press)

Kato, Y. and Nevins, D. J. (1984) Enzymic dissociation of Zea shoot cell wall polysaccharides. II. Dissociation of (1-3), (1-4)-β-D-glucan by purified (1-3), (1-4)-β-D-glucan-4-glucanohydrolase from Bacillus subtilis. *Plant Physiol.* 75: 745–752.

Labrador, E. and Nevins, D. J. (1990) An exo-β-D-glucanase derived from Zea coleoptile walls with a capacity to elicit cell elongation. *Physiol. Plant.* 77: 479–486.

Laemmli, U. K. (1970) Cleavage of structural proteins during the assembly of the head of bacteriophage T4. *Nature* 227: 680–685.

Li, CD, Langridge, P., Lance, R., Xu, P., Fincher, GB (1996) Seven members of the (1–3)-beta-glucanase gene family in barley (hordelun vulgare) are clustered on the long arm of chromosome 3 (3hl). *Theoretical and Applied Genetics.* 92: 791–796.

Loescher, W. and Nevins, D. J. (1972) Auxin-induced changes in Avena coleoptile cell wall composition. *Plant Physiol.* 50: 556–563.

Loescher, W. and Nevins, D. J. (1973) Turgor-dependent changes in Avena coleoptile cell wall composition. *Plant Physiol.* 52: 248–251.

Luttenegger, D. G. and Nevins, D. J. (1985) Transient nature of a (1-3),(1-4)- β-D-glucan in Zea mays coleoptile cell walls. *Plant Physiol.* 77: 175–178.

Masuda, Y. (1990) Auxin-induced cell elongation and cell wall changes. *Bot Mag. Tokyo* 103: 345–370.

Mrmova, M., A. J. Harvey, J. Wang, N. J. Shirley, G. P. Jones, B. A. Stone, P. B. Hoj, and G. B. Fincher: Barley β-D-glucan exohydrolases with β-D-glucosidase activity. Purification, characterization, and determination of primary structure from a cDNA clone. *J. Biol. Chem.* 271, 5277–5286 (1996).

Mundy, J. and Fincher, G. B. (1986) Effects of gibberellic acid and abscisic acid on levels of translatable mRNA (1–3,1–4)- β-D-glucanase in barley aleurone. *FEBS Lett.* 198: 349–352.

Nevins, D. J. (1992) Antibodies as probes for identifying mechanisms responsible for cell elongation. In Current Topics in Plant Biochemistry and Physiology, vol. 11. Edited by Randal, D. D., Sharp R. E., Novacky A. J., and Belvins D. G., Univ. Missouri, Columbia, pp 86–96.

Nevins, D. J., Hatfield, R., Hoson, T. and Inouhe, M. (1987) Inhibition of elongation by antibodies specific for wall proteins. In Physiology of Cell Expansion during Plant Growth. Edited by Cosgrove, D. J. and Knieval, D. P., The American Society for Plant Physiologists, Rockville, pp 122–132.

Nishitani, K. and Tominaga, R. (1992) Endo-xyloglucan transferase, a novel class of glycosyltransferase that catalyzes transfer of a segment of xyloglucan molecule to another xyloglucan molecule. *J. Biol. Chem.* 267: 21058–21064.

O'Neill, R. A. and Scott, T. K. (1987) Rapid effects of IAA on cell surface proteins from intact carrot suspension culture cells. *Plant Physiol.* 84: 443–446.

Rodriguez, R L, Litts, J C, Thomas, B R (1997) Characterization of HV34, an endo-beta-glucanase gene from barley (Accession No. U96096) (PGR 970172). *Plant Physiol.* 115: 1729

Romero, GO, Simmons, C., Yaneshita, M., Doan, M., Thomas, BR, Rodriguez, RL (1998) Characterization of rice endo-b-glucanase genes (Gns2–Gns14) defines a new subgroup within the gene family. *Gene* (in press)

Sakurai, N. (1991) Cell wall functions in growth and development. A physical and chemical point of view. *Bot Mag. Tokyo* 104: 235–251.

Sakurai, N. and Masuda, Y. (1977) Effect of indole-3-acetic acid on cell wall loosening: Changes in mechanical properties and noncellulosic glucose content of Avena coleoptile cell wall. *Plant Cell Physiol.* 18: 587–594.

Sakurai, N. and Masuda, Y. (1978a) Auxin-induced changes in barley coleoptile cell wall composition. *Plant Cell Physiol.* 19: 1217–1223.

Sakurai, N. and Masuda, Y. (1978b) Auxin-induced extension, cell wall loosening and changes in the wall polysaccharide content of barley coleoptile segments. *Plant Cell Physiol.* 19: 1225–1233.

Sakurai, N., Nishitani, K. and Masuda, Y. (1979) Auxin-induced changes in the molecular weight of hemicellulosic polysaccharides of Avena coleoptile cell wall. *Plant Cell Physiol.* 20: 1349–1357.

Simmons, C. R.: The physiology and molecular biology of plant (1->3)- β-D-glucanase and (1->3,1->4) β-D-glucanases. *Critical Reviews in Plant Sciences* 13,325–387 (1994)

Slakeski, N. and Fincher, G. B. (1992a) Developmental regulation of (1–3,1–4)- β-D-glucanase gene expression in barley. *Plant Physiol.* 99: 1226–1231.

Slakeski, N. and Fincher, G. B. (1992b) Barley (1–3,1–4)-β-D-glucanase isoenzyme E1 gene expression is mediated by auxin and gibberellic acid. *FEBS Lett.* 306: 98–102.

Somogy, M. (1952) Note on sugar determinations. *J. Biol. Chem.* 195: 19–23.

Stuart, I. M., Loi, L. and Fincher, G. B. (1986) Development of (1–3,1–4)- β-D-glucan endohydrolase isoenzymes in isolated scutella and aleurone layers of barley (Hordium vulgare). *Plant Physiol.* 80: 310–314.

Taiz, L. (1984) Plant cell expansion: Regulation of cell wall mechanical properties. *Annu. Rev. Plant Physiol.* 35: 585–657.

Yamrnamoto, R., Inouhe, M. and Masuda, Y. (1988) Galactose inhibition of auxin-induced growth of mono- and dicotyledonous plants. *Plant Physiol.* 86: 1223–1227.

Zarra, I. and Masuda, Y. (1979) Growth and cell wall changes in rice coleoptiles growing under different conditions. I. Changes in turgor pressure and cell wall polysaccharides during intact growth. *Plant Cell Physiol* 20: 1117–1124.

Zarra, I. and Masuda, Y. (1979) Growth and cell wall changes in rice coleoptiles growing under different conditions. II. Auxin-induced growth in coleoptile segments. *PlantCellPhysiol.* 20: 1125–1133.

---

What is claimed is:

1. An isolated nucleic acid encoding endo-1,3;1,4-β-glucanase comprising a polynucleotide selected from the group consisting of:
   (a) a polynucleotide that encodes the polypeptide of SEQ ID NO: 2;
   (b) a polynucleotide encoding a polypeptide having at least 95% sequence identity to SEQ ID NO: 2, wherein the % sequence identity is based upon the entire sequence and is determined by BLAST 2.0 under default parameters;
   (c) a polynucleotide comprising the sequence set forth in SEQ ID NO: 1; and
   (d) a polynucleotide complementary to a polynucleotide of (a) through (c) wherein said nucleic acid encodes a polypeptide that hydrolyzes beta-glucans.

2. A vector comprising at least one nucleic acid of claim 1.

3. A recombinant expression cassette, comprising the nucleic acid of claim 1 operably linked to a promoter, wherein the nucleic acid is in the sense or antisense orientation.

4. A host cell comprising the recombinant expression cassette of claim 3.

5. A transgenic plant cell comprising the recombinant expression cassette of claim 3.

6. A transgenic plant comprising the recombinant expression cassette of claim 3.

7. The transgenic plant of claim 6, wherein the plant is a plant selected from the group consisting of maize, soybean, sunflower, sorghum, canola, wheat, alfalfa, cotton, rice, barley, and millet.

8. A transgenic seed from the transgenic plant of claim 7.

9. A method of modulating the level of endoglucanase protein in a plant, comprising;
   (a) introducing into a plant a recombinant expression cassette comprising the nucleic acid of claim 1 operably linked to a promoter;
   (b) regenerating the plant cell to produce a regenerated plant, thereby inducing expression of said polynucleotide for a time sufficient to modulate endoglucanase protein in said plant.

10. The method of claim 9, wherein the plant is a plant selected from the group consisting of maize, soybean, sunflower, sorghum, canola, wheat, alfalfa, cotton, rice, barley, and millet.

11. The method of claim 9, wherein the level of endoglucanase protein is increased.

* * * * *

SEQUENCE LISTING

```
<160> NUMBER OF SEQ ID NOS: 3

<210> SEQ ID NO 1
<211> LENGTH: 1091
<212> TYPE: DNA
<213> ORGANISM: Zea mays
<220> FEATURE:
<223> OTHER INFORMATION: maize coleoptile endo-1,3;1,4-beta
      glucanase cDNA
<220> FEATURE:
<221> NAME/KEY: CDS
<222> LOCATION: (68)..(979)
<223> OTHER INFORMATION: endo-1,3;1,4-beta glucanase

<400> SEQUENCE: 1
agcccacaac cattattctt attccactgc atcaggtcca agtccaactc tccaagcggc         60 aagcgcc atg cct tct tcc gcg cag gtt ctg ctc tgc ctc gcc gcc gtg         109
        Met Pro Ser Ser Ala Gln Val Leu Leu Cys Leu Ala Ala Val
          1               5                  10 ctg gcg gcg gcg gcg gcc acc acc gcc gag gcg cac tcg cag tgc ctg         157
Leu Ala Ala Ala Ala Ala Thr Thr Ala Glu Ala His Ser Gln Cys Leu
```

```
                15                  20                  25                  30
gac aac ccg ccg gac cgg tcc atc cac ggc cgc cag ctg gcc gag gcc      205
Asp Asn Pro Pro Asp Arg Ser Ile His Gly Arg Gln Leu Ala Glu Ala
                35                  40                  45 ggc gag gtc gtc cac gac ctc ccc ggt ggc ctc agg gcc tac gtc agc      253
Gly Glu Val Val His Asp Leu Pro Gly Gly Leu Arg Ala Tyr Val Ser
            50                  55                  60 ggc gcc gcg agc tcg agc cgc gcc gtc gtc ctc gcc tcc gac gtc ttc      301
Gly Ala Ala Ser Ser Ser Arg Ala Val Val Leu Ala Ser Asp Val Phe
        65                  70                  75 ggg tac gag gcg cca ttg ctc aga cag ata gta gac aag gtt gca aag      349
Gly Tyr Glu Ala Pro Leu Leu Arg Gln Ile Val Asp Lys Val Ala Lys
    80                  85                  90 gca ggg tac ttc gtc gtc gtg ccc gat ttc ttg aag gga gac tac tta      397
Ala Gly Tyr Phe Val Val Val Pro Asp Phe Leu Lys Gly Asp Tyr Leu
95                  100                 105                 110 gac gac aag aaa aac ttt aca gaa tgg ctc gag gct cac tct ccg gtg      445
Asp Asp Lys Lys Asn Phe Thr Glu Trp Leu Glu Ala His Ser Pro Val
                115                 120                 125 aaa gct gcg gaa gac gct aag cca ctg ttc gcc gct ttg aag aag gaa      493
Lys Ala Ala Glu Asp Ala Lys Pro Leu Phe Ala Ala Leu Lys Lys Glu
            130                 135                 140 ggg aag tcc gtc gcg gtg gga ggc tac tgc tgg gga ggg aag ctg agc      541
Gly Lys Ser Val Ala Val Gly Gly Tyr Cys Trp Gly Gly Lys Leu Ser
        145                 150                 155 gtg gag gtg ggg aag acc agc gac gtc aaa gct gtg tgc ctt tcg cac      589
Val Glu Val Gly Lys Thr Ser Asp Val Lys Ala Val Cys Leu Ser His
    160                 165                 170 ccg tac agc gtc act gcc gac gac atg aaa gag gtg aaa tgg ccg atc      637
Pro Tyr Ser Val Thr Ala Asp Asp Met Lys Glu Val Lys Trp Pro Ile
175                 180                 185                 190 gag atc ctg ggg gcc cag aac gac acg acc acg ccg ccg aaa gaa gtg      685
Glu Ile Leu Gly Ala Gln Asn Asp Thr Thr Thr Pro Pro Lys Glu Val
                195                 200                 205 tac cgg ttc gtg cat gtg ctg cgt gaa aga cac gag gtt ccc ttt cgc      733
Tyr Arg Phe Val His Val Leu Arg Glu Arg His Glu Val Pro Phe Arg
            210                 215                 220 cgt caa gac cgc aga gac ggc cct cgc cta cat ggt cag ctg gtt caa      781
Arg Gln Asp Arg Arg Asp Gly Pro Arg Leu His Gly Gln Leu Val Gln
        225                 230                 235 caa gca cct caa ctg aat gaa gcc tgc act gca ccc acc aga ctg aat      829
Gln Ala Pro Gln Leu Asn Glu Ala Cys Thr Ala Pro Thr Arg Leu Asn
    240                 245                 250 tca ata aac cac agc agt gct gtg ata ttt tgt ttc gat tcg tgg ctc      877
Ser Ile Asn His Ser Ser Ala Val Ile Phe Cys Phe Asp Ser Trp Leu
255                 260                 265                 270 ccc aga ttg att ttc atg gct acg acc tct tct act act gta att tcc      925
Pro Arg Leu Ile Phe Met Ala Thr Thr Ser Ser Thr Thr Val Ile Ser
                275                 280                 285 ctc att ttt ttt gtc tct atg tat ttc ttt tct ttt ctt ttt gct ttt      973
Leu Ile Phe Phe Val Ser Met Tyr Phe Phe Ser Phe Leu Phe Ala Phe
            290                 295                 300 tta tgatcgcaat aaagttcagt agggtaaaa aaaaaaaaa aaaaaaaaa             1026
Leu aaaaaaaaaa aaaaaaaaa aaaaaaaaaa aaaaaaaaa aaaaaaaaaa aaaaaaaaaa     1086
aaaaa                                                              1091

<210> SEQ ID NO 2
```

```
<211> LENGTH: 303
<212> TYPE: PRT
<213> ORGANISM: Zea mays
<220> FEATURE:
<223> OTHER INFORMATION: maize coleoptile endo-1,3;1,4-beta glucanase

<400> SEQUENCE: 2

Met Pro Ser Ser Ala Gln Val Leu Leu Cys Leu Ala Ala Val Leu Ala
 1               5                  10                  15

Ala Ala Ala Ala Thr Thr Ala Glu Ala His Ser Gln Cys Leu Asp Asn
            20                  25                  30

Pro Pro Asp Arg Ser Ile His Gly Arg Gln Leu Ala Glu Ala Gly Glu
        35                  40                  45

Val Val His Asp Leu Pro Gly Gly Leu Arg Ala Tyr Val Ser Gly Ala
    50                  55                  60

Ala Ser Ser Arg Ala Val Leu Ala Ser Asp Val Phe Gly Tyr
65                  70                  75                  80

Glu Ala Pro Leu Leu Arg Gln Ile Val Asp Lys Val Ala Lys Ala Gly
                85                  90                  95

Tyr Phe Val Val Val Pro Asp Phe Leu Lys Gly Asp Tyr Leu Asp Asp
            100                 105                 110

Lys Lys Asn Phe Thr Glu Trp Leu Glu Ala His Ser Pro Val Lys Ala
        115                 120                 125

Ala Glu Asp Ala Lys Pro Leu Phe Ala Ala Leu Lys Lys Glu Gly Lys
    130                 135                 140

Ser Val Ala Val Gly Gly Tyr Cys Trp Gly Gly Lys Leu Ser Val Glu
145                 150                 155                 160

Val Gly Lys Thr Ser Asp Val Lys Ala Val Cys Leu Ser His Pro Tyr
                165                 170                 175

Ser Val Thr Ala Asp Asp Met Lys Glu Val Lys Trp Pro Ile Glu Ile
            180                 185                 190

Leu Gly Ala Gln Asn Asp Thr Thr Thr Pro Pro Lys Glu Val Tyr Arg
        195                 200                 205

Phe Val His Val Leu Arg Glu Arg His Glu Val Pro Phe Arg Arg Gln
    210                 215                 220

Asp Arg Arg Asp Gly Pro Arg Leu His Gly Gln Leu Val Gln Gln Ala
225                 230                 235                 240

Pro Gln Leu Asn Glu Ala Cys Thr Ala Pro Thr Arg Leu Asn Ser Ile
                245                 250                 255

Asn His Ser Ser Ala Val Ile Phe Cys Phe Asp Ser Trp Leu Pro Arg
            260                 265                 270

Leu Ile Phe Met Ala Thr Thr Ser Ser Thr Thr Val Ile Ser Leu Ile
        275                 280                 285

Phe Phe Val Ser Met Tyr Phe Phe Ser Phe Leu Phe Ala Phe Leu
    290                 295                 300

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence:Sal-A20
      oligonucleotide

<400> SEQUENCE: 3
tcgacccacg cgtccgaaaa aaaaaaaaaa aaaaaa                                 36
```